(12) United States Patent
Maruo et al.

(10) Patent No.: US 7,964,077 B2
(45) Date of Patent: Jun. 21, 2011

(54) AUTOMATED TWO-DIMENSIONAL ELECTROPHORESIS APPARATUS AND INSTRUMENT CONSTITUTING THE APPARATUS

(75) Inventors: Yuji Maruo, Nagareyama (JP); Katsuyoshi Takahashi, Setagaya-ku (JP); Yutaka Unuma, Matsudo (JP); Keisuke Usui, Tsukuba (JP); Hideki Kinoshita, Tsukuba (JP); Kisho Shiseki, Tsukuba (JP); Yoshio Suzuki, Tsukuba (JP); Atsunori Hiratsuka, Tsukuba (JP); Hiroyuki Fukui, Tsukuba (JP); Kenji Yokoyama, Tsukuba (JP); Ichiji Namatame, Chuo-ku (JP); Kouhei Yodoya, Chuo-ku (JP); Yasuhiro Ogawa, Chuo-ku (JP); Koji Sakairi, Taito-ku (JP); Chie Hayashida, Taito-ku (JP); Satonari Akutsu, Sagamihara (JP); Kazuyoshi Yano, Shibuya-ku (JP); Isao Karube, Yokohama (JP)

(73) Assignees: Sharp Kabushiki Kaisha, Osaka (JP); Toppan Printing Co., Ltd, Tokyo (JP)

( * ) Notice: Subject to any disclaimer, the term of this patent is extended or adjusted under 35 U.S.C. 154(b) by 984 days.

(21) Appl. No.: 11/510,838

(22) Filed: Aug. 28, 2006

(65) Prior Publication Data
US 2007/0045118 A1    Mar. 1, 2007

(30) Foreign Application Priority Data
Aug. 31, 2005  (JP) ................................. 2005-252755

(51) Int. Cl.
*G01N 27/26*   (2006.01)
*G01N 27/447*  (2006.01)

(52) U.S. Cl. ........ 204/600; 204/459; 204/548; 204/605; 204/606; 204/610; 204/456; 204/461; 204/466

(58) Field of Classification Search .................. 204/548, 204/456–469, 600–610
See application file for complete search history.

(56) References Cited

U.S. PATENT DOCUMENTS 4,573,254 A * 3/1986 Kirk et al. .................... 29/564.8
(Continued)

FOREIGN PATENT DOCUMENTS
JP    54-21796    2/1979
(Continued)

OTHER PUBLICATIONS

U.S. Patent Office mailed Oct. 28, 2009 in co-pending application U.S. Appl. No. 11/852,376.
(Continued)

Primary Examiner — Alexa D Neckel
Assistant Examiner — Jennifer Dieterle
(74) Attorney, Agent, or Firm — Nixon & Vanderhye P.C.

(57) ABSTRACT

The present invention is to provide a sample separation instrument used in a sample separation apparatus which includes: holding means for holding a first medium supporter which supports a first medium; and driving means for moving fixing means or the holding means in a direction parallel or perpendicular to a plane whose sides extend in the first direction and in the second directions. The sample separation instrument includes an insulator for storing a second medium which allows a sample separated in the first medium in the first direction to be further separated in the second direction different from the first direction, wherein: the insulator includes a first opening and a second opening each of which defines the second direction in which the second medium is electrified, and the second opening has a shape which allows the first medium containing the separated sample to be attached to the second medium along the first direction. The present invention realizes automation of the two-dimensional electrophoresis to enhance the convenience of the two-dimensional electrophoresis, to less depend on the operator's skill, and to enhance the reproducibility of the electrophoresis result.

33 Claims, 11 Drawing Sheets

U.S. PATENT DOCUMENTS

| | | | |
|---|---|---|---|
| 4,666,581 A * | 5/1987 | Itoh et al. | 204/616 |
| 5,087,423 A | 2/1992 | Ishibashi | |
| 5,292,420 A | 3/1994 | Nakamura | |
| 5,296,115 A | 3/1994 | Rocklin et al. | |
| 5,407,546 A | 4/1995 | Schickle | |
| 5,472,584 A | 12/1995 | Rocklin et al. | |
| 5,627,022 A | 5/1997 | Renfrew et al. | |
| 5,773,645 A | 6/1998 | Hochstrasser | |
| 5,876,670 A | 3/1999 | Mitsumaki et al. | |
| 5,885,431 A | 3/1999 | Renfrew et al. | |
| 6,013,165 A | 1/2000 | Wiktorowicz et al. | |
| 6,277,259 B1 * | 8/2001 | Guttman et al. | 204/461 |
| 6,328,870 B1 * | 12/2001 | Provonchee et al. | 204/616 |
| 6,376,231 B1 | 4/2002 | Enomoto et al. | |
| 6,827,902 B1 | 12/2004 | Kuriyama et al. | |
| 6,867,851 B2 * | 3/2005 | Blumenfeld et al. | 356/73 |
| 7,077,940 B2 | 7/2006 | Ingenhoven et al. | |
| 2002/0041377 A1 * | 4/2002 | Hagiwara et al. | 356/399 |
| 2002/0133300 A1 * | 9/2002 | Anderson et al. | 702/19 |
| 2002/0151076 A1 * | 10/2002 | Anderson et al. | 436/43 |
| 2003/0116497 A1 * | 6/2003 | Carlson et al. | 210/435 |
| 2003/0221962 A1 | 12/2003 | Ingenhoven et al. | |
| 2005/0139470 A1 | 6/2005 | Sze | |
| 2007/0045118 A1 | 3/2007 | Maruo et al. | |
| 2008/0067079 A1 | 3/2008 | Takahashi et al. | |
| 2008/0296158 A1 | 12/2008 | Maruo et al. | |

FOREIGN PATENT DOCUMENTS

| | | |
|---|---|---|
| JP | 58-21555 A | 2/1983 |
| JP | 59-107253 | 6/1984 |
| JP | 61-104248 A | 5/1986 |
| JP | 1-260356 A | 10/1989 |
| JP | 3-242547 A | 10/1991 |
| JP | 4-303756 A | 10/1992 |
| JP | 10-512043 A | 11/1998 |
| JP | 11-316237 A | 11/1999 |
| JP | 2000-298116 A | 10/2000 |
| JP | 2004-69387 A | 3/2004 |
| JP | 2004-155687 | 6/2004 |
| JP | 2005-233908 A | 9/2005 |
| WO | 2006/085539 A1 | 8/2006 |

OTHER PUBLICATIONS

"Electrophoresis Latest Protocol", Separate Volume, Experimental Medicine, The Protocol Series, Jan. 1, 2000, pp. 77-83 and partial English translation thereof.

Office Action mailed Apr. 29, 2010, for U.S. Appl. No. 11/852,376.

Office Action mailed Jul. 21, 2010, for U.S. Appl. No.11/852,376.

Office Action mailed Dec. 22, 2010, for U.S. Appl. No. 11/852,376.

P.C. Hauser et al. "New Zealand—Anion detection in capillary electrophoresis with ion-selective microelectrodes"—Abstract, Biosensors & Bioelectronics, vol. 10, No. 1/2 ,1 page, (1995).

* cited by examiner

US 7,964,077 B2

AUTOMATED TWO-DIMENSIONAL ELECTROPHORESIS APPARATUS AND INSTRUMENT CONSTITUTING THE APPARATUS

This Nonprovisional application claims priority under 35 U.S.C. §119(a) on Patent Application No. 252755/2005 filed in Japan on Aug. 31, 2005, the entire contents of which are hereby incorporated by reference.

FIELD OF THE INVENTION

The present invention relates to an automated biological sample separation apparatus, an instrument constituting the separator, and usage thereof. More specifically, the present invention relates to an automated two-dimensional electrophoresis apparatus, an instrument constituting the apparatus, and a two-dimensional electrophoresis method.

BACKGROUND OF THE INVENTION

After completion of the human genome project, the study of proteome (proteomics) has been widely practiced. The term "proteome" is used to describe the entire complement of proteins which are generated in a given biological organism or system based on translation. Examples of the proteomics include protein profiling and a similar study.

One of the most popular techniques adopted as the protein profiling is protein two-dimensional electrophoresis. Proteins have unique properties in electric charge and a molecular weight. Thus, in separating respective proteins from the proteome which is a mixture of a large number of proteins, it is possible to separate a larger number of proteins with high resolution by depending on both the electric charge and the molecular weight than depending on only the electric charge or only the molecular weight.

The two-dimensional electrophoresis includes two electrophoresis steps, i.e., (i) isoelectric focusing electrophoresis in which proteins are separated depending on electric charge and (ii) slabgel electrophoresis in which proteins are separated depending on a molecular weight (particularly, SDS-PAGE). Furthermore, the two-dimensional electrophoresis can be performed using a sample in the presence of or in the absence of denaturant. This is an excellent technique which allows several hundreds or more kinds of proteins to be separated at once (for example, see Patent Document 1 and Non Patent Document 1).
[Patent Document 1]
Japanese Laid-Open Patent Publication No. 30605/1999 (Tokukaihei 11-30605)(Publication date: Feb. 2, 1999)
[Non Patent Document 1]
"Electrophoresis Latest Protocol for More Quantitative Detection Analysis with Higher Sensitivity, Ranging from General Operation to Genomics And Proteomics!" (p 55-108: published by YODOSHA CO., LTD. in 2000)

The two-dimensional electrophoresis is performed as follows. A sample is subjected to isoelectric focusing electrophoresis in a first dimensional gel, and the first dimensional gel is retrieved and is applied to a second dimensional gel, and then separation in the second dimensional gel is performed on the basis of a molecular weight. Generally, the first dimensional gel in which the isoelectric focusing electrophoresis is performed is extremely thin compared with its width and length. Thus, it is difficult to discriminate front and rear faces and pH gradient directions of the gel. Furthermore, warpage and twist are likely to occur, so that it is difficult to keep its shape constant. This tends to cause low reproducibility of an electrophoresis result. Also, it is not easy to treat the first dimensional gel, so that it is difficult to enhance positional accuracy in moving the first dimensional gel to the second dimensional gel. In case of using SDS-PAGE to perform separation in the second dimensional gel, it is necessary to perform equilibration (SDS process and reduction: process with drug solution) in order to develop proteins of the first dimensional gel into the second dimension after finishing the electrophoresis in the first dimensional gel. The necessity to perform such a process with respect to the first dimensional gel causes uneven operations of different operators.

In this way, the two-dimensional electrophoresis is an excellent technique but requires a lot of skill. This technique depends on the skill of the operator, so that it is difficult to obtain quantitative data with high reproducibility by adopting the two-dimensional electrophoresis.

The present invention was made in view of the foregoing problems, and an object of the present invention is to enhance the convenience of the two-dimensional electrophoresis, to less depend on the operator's skill, and to enhance the reproducibility of the electrophoresis result. Specifically, an object of the present invention is to automate the two-dimensional electrophoresis.

SUMMARY OF THE INVENTION

An object of the present invention is to provide a sample separation apparatus and a sample separation apparatus constituting instrument (sample separation instrument) for realizing the automation.

In order to achieve the object, a sample separation instrument according to the present invention includes an insulator for storing a second medium which allows a sample separated in a first medium in a first direction to be further separated in a second direction different from the first direction, wherein: the insulator includes a first opening and a second opening each of which defines the second direction in which the second medium is electrified, and the second opening has a shape which allows the first medium containing the separated sample to be attached to the second medium along the first direction.

The second opening has the foregoing shape, so that the sample separation instrument according to the present invention allows a sample contained in the first medium to favorably move into the second medium. As a result, it is possible to perform the two-dimensional electrophoresis having excellent resolution. Further, if the foregoing arrangement is adopted, the sample separation instrument according to the present invention allows the first medium to be safely attached to the second medium without stopping application of a high voltage, and then it is possible to remove the first medium as required.

A sample separation apparatus according to the present invention includes fixing means, wherein: the fixing means fixes thereon a sample separation instrument having an insulator for storing a second medium which allows a sample separated in a first medium in a first direction to be further separated in a second direction different from the first direction, and the insulator includes a first opening and a second opening each of which defines the second direction in which the second medium is electrified, and the second opening has a shape which allows the first medium containing the separated sample to be attached to the second medium along the first direction.

If the foregoing arrangement is adopted, various steps can be performed more stably in the sample separation apparatus according to the present invention.

Additional objects, features, and strengths of the present invention will be made clear by the description below. Further, the advantages of the present invention will be evident from the following explanation in reference to the drawings.

DESCRIPTION OF THE EMBODIMENTS

Figure 1:
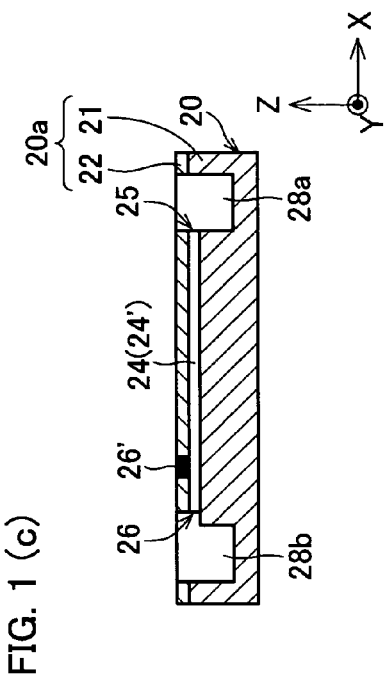
FIG. 1(a) is an oblique perspective view illustrating essential components of an automated two-dimensional electrophoresis apparatus according to one embodiment of the present invention.
FIG. 1(b) is a side view illustrating an arrangement of instruments constituting the automated two-dimensional electrophoresis apparatus according to one embodiment of the present invention.
FIG. 1(c) is a cross sectional view of an instrument constituting the automated two-dimensional electrophoresis apparatus according to one embodiment of the present invention.
FIG. 1(d) is a top view of the instrument constituting the automated two-dimensional electrophoresis apparatus according to one embodiment of the present invention.
Figure 1:
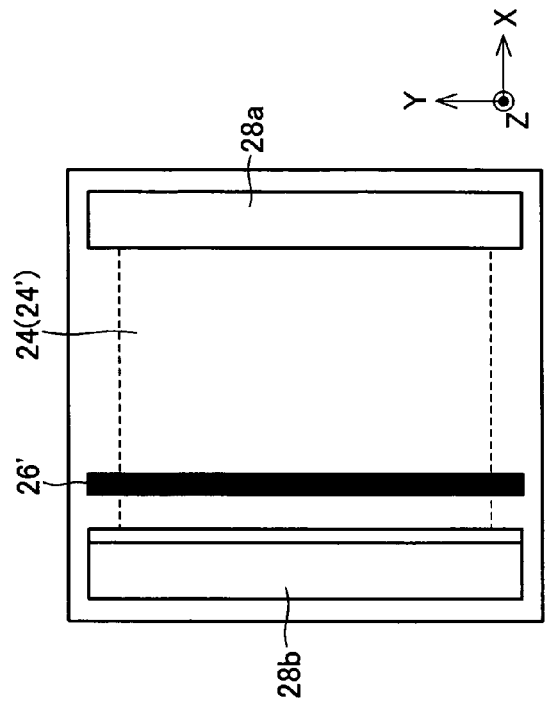
Figure 1:
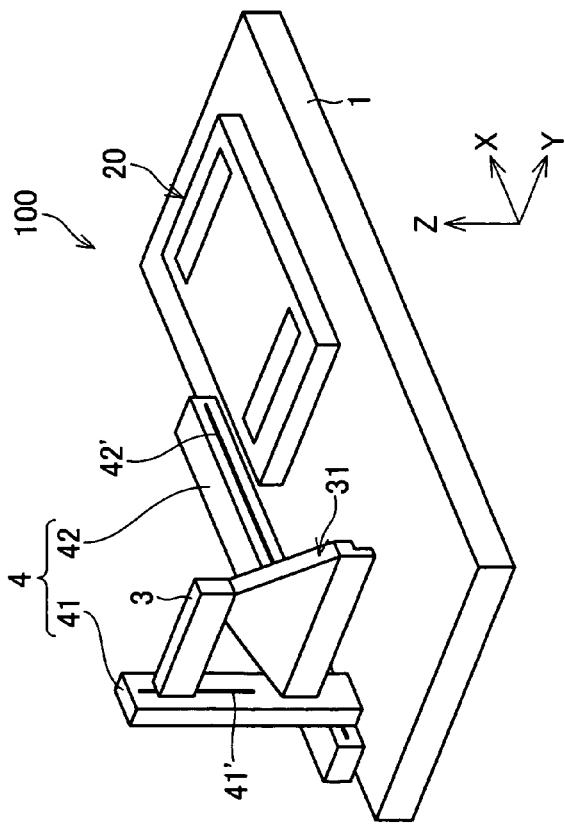
Figure 1:
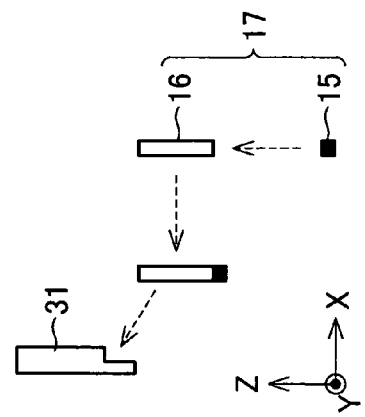

The following describes one embodiment of the sample separation apparatus according to the present invention by explaining an automated two-dimensional electrophoresis apparatus 100 as an example.

FIG. 1(a) is an oblique perspective view illustrating essential components of the automated two-dimensional electrophoresis apparatus 100. FIG. 1(b) illustrates an arrangement in which a first medium 15 is combined to an arm 31 of holding means 3 via a first medium supporter 16. FIG. 1(c) and FIG. 1(d) are respectively a cross sectional view and a top view each of which illustrates an arrangement of a second separation section (sample separation instrument) 20 used in the automated two-dimensional electrophoresis apparatus 100.

The automated two-dimensional electrophoresis apparatus 100 according to the present embodiment includes: fixing means 1 for fixing the second separation section (sample separation instrument) 20 for performing second dimensional separation with respect to a sample; holding means 3 having the arm 31 for holding a gel-attached supporter 17 supporting the first medium 15 for performing first dimensional separation; and driving means 4 (41 and 42) for moving the fixing means 1 and/or the holding means 3 so as to change a relative position of the fixing means 1 and the holding means 3.

In the automated two-dimensional electrophoresis apparatus 100, the sample is separated in a first direction (Y direction in the figure) at a first separation section (not shown), and the separated sample is subsequently carried and attached to a second opening 26 of the second separation section 20, and then the attached sample is separated in a second direction (X direction in the figure) at the second separation section 20.

The second opening section 26 has the following shape. As illustrated in FIG. 1(c) and FIG. 1(d), a second buffer solution chamber 28b has an opening which penetrates an upper insulating plate 22 so that a width of the opening is wider than a groove width of a lower insulating plate 21 corresponding thereto. The width difference allows the first medium 15 and a second medium 24 to be in tightly contact with each other, so that it is possible to favorably perform the second dimensional separation with respect to the sample in the first medium 15 which has subjected to the first dimensional separation.

In order to attach the first medium 15 containing the separated sample to the second medium 24, an insulator 20a covering the second medium 24 has to include a portion which allows the first medium 15 and the second medium 24 to be in tightly contact with each other. Such a portion may be the second opening 26 or may be another opening (third opening) 26' provided between a first opening 25 and the second opening 26. A first medium supplying inlet has a size and a shape which are suitable for attaching the first medium 15 containing the separated sample to the second medium 24 so that an attached face is in a direction perpendicular to the first direction.

In case where the second separation section 20 includes the second medium 24 therein, it is preferable that the second medium 24 protrudes from the second opening 26 so that the first medium 15 and the second medium 24 are in tightly contact with each other at a first medium supplying section, and it is more preferable that the second medium protruding from the second opening 26 is free from any bump so that both the mediums are in more tightly contact with each other. Note that, in case where the second medium 24 does not protrude from the second opening 26, an attaching member (not shown) is provided on the second opening 26 so as to keep the first medium 15 and the second medium 24 in tightly contact with each other. Preferable examples of the attaching member include agarose, gel such as acrylamide having low viscosity (1 to 3%), high viscosity liquid such as glycerin, polyethyleneglycol, and hydroxypropylcellulose. However, the attaching member is not limited to them.

A parameter for defining the separation in the first direction (Y direction in the figure) and a parameter for defining the separation in the second direction (X direction in the figure) may be identical to each other, but it is preferable that these parameters are different from each other so as to improve the separating performance. Examples of the parameters for defining the separation in both the directions include: an isoelectric point of a protein or the like; a molecular weight; a surface charge per a unit size (zonal electrophoresis); a coefficient of distribution into the micelle (micelle electromotive chromatography); a coefficient of distribution from a stationary phase into a mobile phase (electric chromatography); an affinity constant with respect to an interacting substance (affinity bond electrophoresis); and a similar parameter. In general two-dimensional electrophoresis, the separation in the first direction is performed in accordance with the isoelectric point and the separation in the second direction is performed in accordance with the molecular weight.

As illustrated in FIG. 1($a$), in the automated two-dimensional electrophoresis apparatus 100, the driving means 4 includes vertical direction driving means 41 and horizontal direction driving means 42. Specifically, the holding means 3 (supporting arm 31) is held by the vertical direction driving means 41 via a trench (holding means coupling section) 41' of the vertical direction driving means 41 so as to be movable in a Z axis direction. Further, the vertical direction driving means 41 is held by the horizontal direction driving means 42 via a trench (Z axis stage coupling section) 42' of the horizontal direction driving means 42 so as to be movable in an X axis direction. Thus, the fixing means 1 and/or the holding means 3 can be moved by the vertical direction driving means 41 in a direction perpendicular to a plane whose sides extend in the first direction and in the second direction and can be moved by the horizontal direction driving means 42 in a direction parallel to the plane whose sides extend in the first direction and in the second direction.

The term "sample" is synonymous of a specimen or a preparation in the field to which the present invention pertains. In case where the term is used in the present specification, the "sample" means a "biological sample" or an equivalent thereof. The "biological sample" means any preparation obtained from a biological material (e.g., individual, liquid, body fluid, cell line, cultured tissue or tissue segment) serving as a source. Examples of the "biological sample" include body fluids (e.g., blood, saliva, dental plaque, blood serum, blood plasma, urine, synovia, and cerebrospinal fluid) and a tissue source. A preferable example of the biological sample is a subject sample. A preferred subject sample is a cutaneous lesions part, sputum, pharyngeal mucus, nasal mucus, purulence, or secreta from the subject. In the present specification, the term "tissue sample" means the biological sample obtained from the tissue source. A method for performing a biopsy of a mammal and obtaining body fluid from the mammal is well known in the field. In the present specification, the term "sample" means not only the biological sample and the tissue sample but also a protein sample extracted from the biological sample and the tissue sample, a genome DNA sample and/or a total RNA sample.

The two-dimensional electrophoresis is described as follows by explaining a case where gel isoelectric focusing electrophoresis is performed in the first dimension and SDS-PAGE is performed in the second dimension. However, the present invention is not limited to this arrangement.

Figure 2:
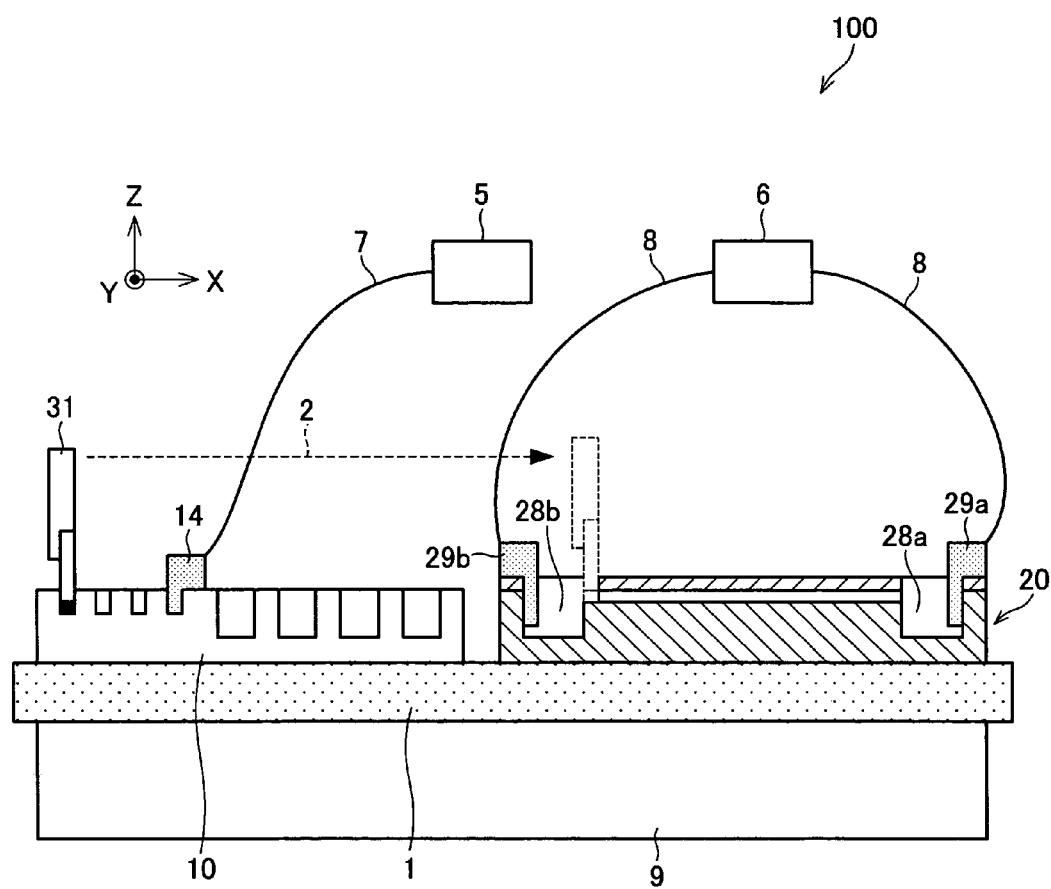
FIG. 2 is a cross sectional view illustrating essential components of the automated two-dimensional electrophoresis apparatus according to one embodiment of the present invention.

In order to automate all the steps, the automated two-dimensional electrophoresis apparatus 100 includes: wiring means 7 for connecting first medium voltage applying means 5 to the first separation section 10; and wiring means 8 for connecting second medium voltage applying means 6 to the second separation section 20, wherein the wiring means 7 has a third electrode 14 (a pair of an anode and a cathode) in its end so that the third electrode 14 is positioned in a first separation chamber 11$d$, and the wiring means 8 has in its ends a first electrode 29$a$ and a second electrode 29$b$ which are respectively positioned in a first buffer solution chamber 28$a$ and a second buffer solution chamber 28$b$ (see FIG. 2).

Figure 11:
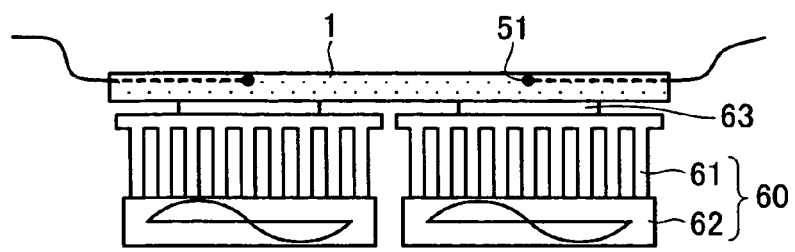
FIG. 11(a) is a schematic illustrating instruments constituting the automated two-dimensional electrophoresis apparatus according to one embodiment of the present invention.
FIG. 11(b) is a schematic illustrating instruments constituting the automated two-dimensional electrophoresis apparatus according to one embodiment of the present invention.
Figure 11:
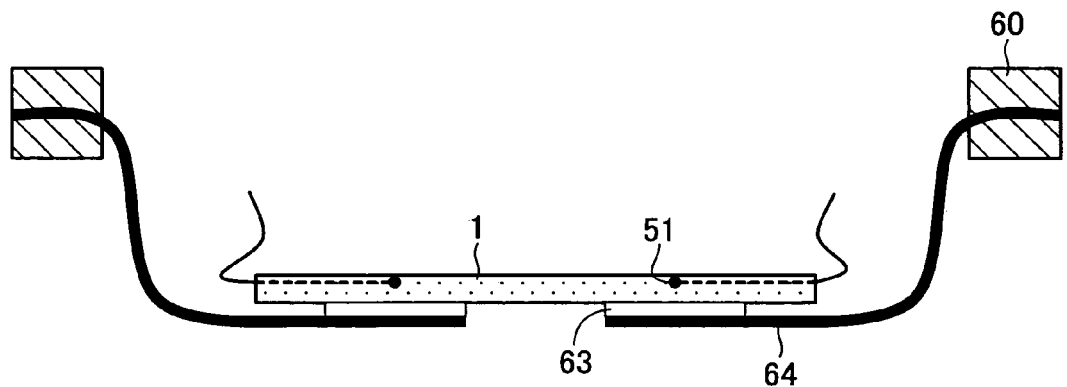

The electrophoresis is performed with a high voltage, so that the first separation section 10 and the second separation section 20 have high temperatures during the sample separation. Thus, in the automated two-dimensional electrophoresis apparatus 100, cooling means 9 (for example, radiating means 60) for cooling (i) the first separation section 10 and the second separation section 20 and (ii) the fixing means 1 for fixing thereon both the separation sections is provided below the fixing means 1. Particularly, the automated two-dimensional electrophoresis apparatus 100 adopts a Peltier cooling control mechanism which includes: the radiating means 60 each of which has a radiating fin 61 and a radiating fan 62; and a cooling Peltier element 63 (see FIG. 11($a$)), so that it is possible to keep the temperatures of the first separation section 10 and the second separation section 20 constant at the time of electrophoresis. FIG. 11($a$) illustrates an arrangement in which a temperature sensor 51 provided by inserting a rhodium into a minute hole monitors surface vicinity temperature of the fixing means 1. In case where the cooling means 9 is not provided below the fixing means 1, the automated two-dimensional electrophoresis apparatus 100 may be arranged so that, for example, heat on a heating face of the Peltier element 63 is transferred via a heat pipe 64 so as to be radiated by the radiating means 60, as illustrated in FIG. 11($b$). If such an arrangement is adopted, the radiating means 60 can be more freely disposed. Additionally, it is possible to dispose the radiating fin and the cooling fan so effectively as not to block flow of hot air which moves upward. Further, a water-cooling pipe utilizing cyclic coolant may be used instead of the heat pipe. The cooling means 9 may be controlled so that the first separation section 10 and the second separation section 20 are kept at the same temperature or may be controlled so that the first separation section 10 and the second separation section 20 are kept at temperatures different from each other. Also, the cooling means 9 may be controlled so that the first separation section 10 and/or the second separation section 20 has not entirely even temperature but different temperatures depending on portions thereof.

FIG. 2 is a cross sectional view of the fixing means 1 and peripheral members of the automated two-dimensional electrophoresis apparatus 100 according to the present embodiment. The two-dimensional electrophoresis is carried out from the left side to the right side in FIG. 2.

In the automated two-dimensional electrophoresis apparatus 100 according to the present embodiment, the first separation section 10 for performing the first dimensional separation with respect to the sample and the second separation section (sample separation instrument) 20 for performing the second dimensional separation with respect to the sample are fixed on the fixing means 1 by vacuum adsorption. The first separation section 10 includes a plurality of chambers, and one of the chambers has an electrode (third electrode) 14. The second separation section 20 includes two chambers (the first buffer solution chamber 28a and the second buffer solution chamber 28b), and electrodes (the first electrode 29a and the second electrode 29b) are provided on the chambers respectively.

As illustrated in FIG. 1(b), the first medium (gel for the isoelectric focusing electrophoresis) 15 used in the first dimensional separation is attached to the first medium supporter 16 so as to constitute the gel-attached supporter 17. To a rear surface of a commercially available first medium, a transparent resin sheet whose thickness is about 0.2 mm adheres, so that the sheet portion and the first medium supporter 16 are bonded to each other with an adhesive. Note that, an adhesive publicly known in the field is used as the foregoing adhesive. However, it is preferable to use an adhesive suitable for reservation at low temperature since the first medium 15 is reserved at low temperature (−20° C.) with it attached to the first medium supporter 16 until the first medium 15 is used. Such a temperature property is applicable to the first medium supporter 16. The first medium supporter 16 is held by the arm 31 which is a part of the holding means 3 (not shown) of the automated two-dimensional electrophoresis apparatus 100. The arm 31 can be moved in the X direction and/or the Z direction, as illustrated in the figure, by the driving means 4 of the automated two-dimensional electrophoresis apparatus 100 according to the present embodiment.

After being combined with the gel-attached supporter 17 by vacuum adsorption, the arm 31 is moved by the driving means 4 in a direction indicated by an arrow 2 of FIG. 2. The gel-attached supporter 17 is moved by the driving means 4, so that the first medium 15 is subjected to a desired process in each chamber provided in the first separation section 10 and is subsequently carried to the second separation section 20.

Note that, the driving means 4 moves the arm 31 as follows. In combination with the vertical direction driving means 41, the horizontal direction driving means 42 drives the arm 31 to a desired position X of a first medium placement chamber 11a, and the driving means 41 subsequently lowers the arm 31 to a desired position Z. By causing the controlling means to control a state in which the gel-attached supporter 17 disposed in the first medium placement chamber 11a adsorbs the arm 31, it is possible to allow the driving means 4 to move the first medium 15. The adsorption to the arm 31 can be automatically controlled by using an electromagnetic valve.

The first medium 15 is extremely thin compared with its width and length. Thus, it is difficult to discriminate front and rear faces and pH gradient directions of the gel. Furthermore, warpage and twist are likely to occur, so that it is difficult to keep its shape constant. This tends to cause low reproducibility of an electrophoresis result. Also, it is not easy to treat the first medium 15 in the respective steps of the electrophoresis, so that it is difficult to enhance positional accuracy in moving the first medium 15. In order to overcome such disadvantage so that it is possible to stably hold and treat the first medium 15 with an automatic device, the inventors of the present invention fixed the first medium 15 on the first medium supporter 16.

Figure 3:
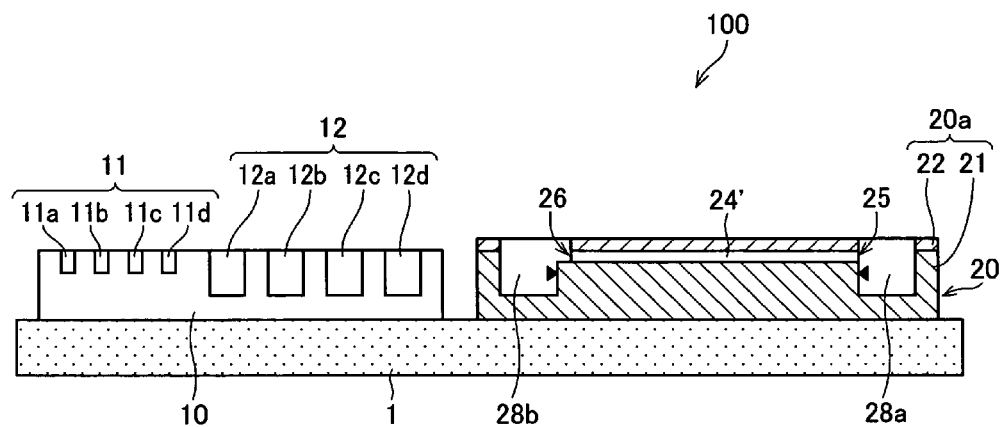
FIG. 3 is a cross sectional view illustrating essential components of the automated two-dimensional electrophoresis apparatus according to one embodiment of the present invention.
Figure 4:
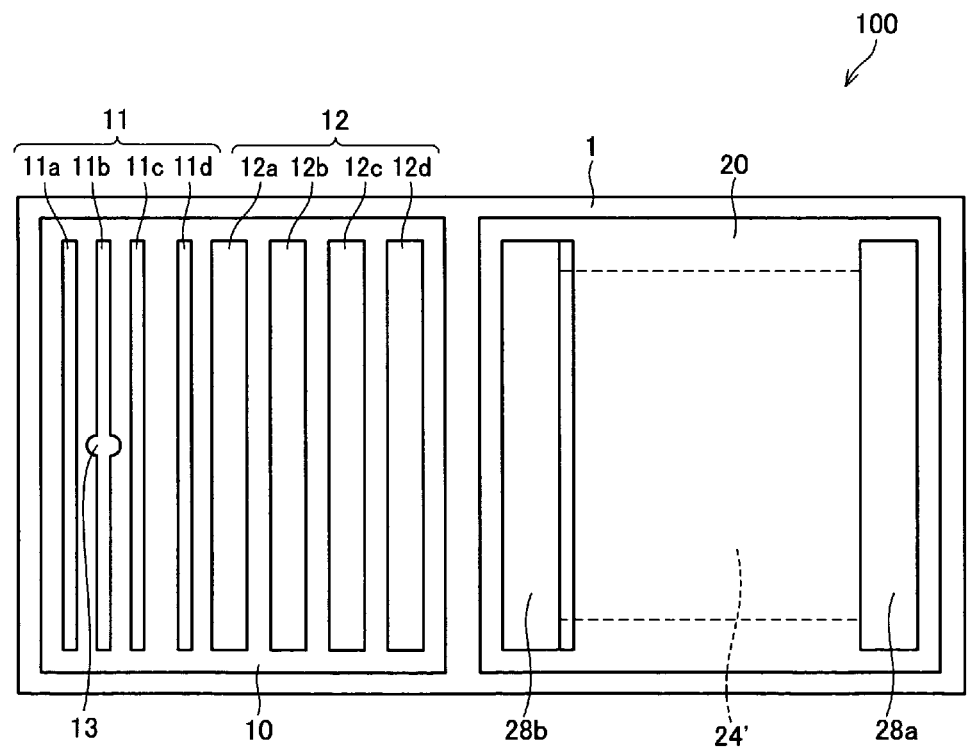
FIG. 4 is a top view illustrating essential components of the automated two-dimensional electrophoresis apparatus according to one embodiment of the present invention.

Arrangements of the first separation section 10 and the second separation section 20 in FIG. 2 are further detailed in FIG. 3 and FIG. 4. FIG. 3 is a cross sectional view of the fixing means 1 on which the first separation section 10 for performing the first dimensional separation with respect to the sample and the second separation section 20 for performing the second dimensional separation with respect to the sample are fixed. FIG. 4 is a top view thereof.

Figure 9:
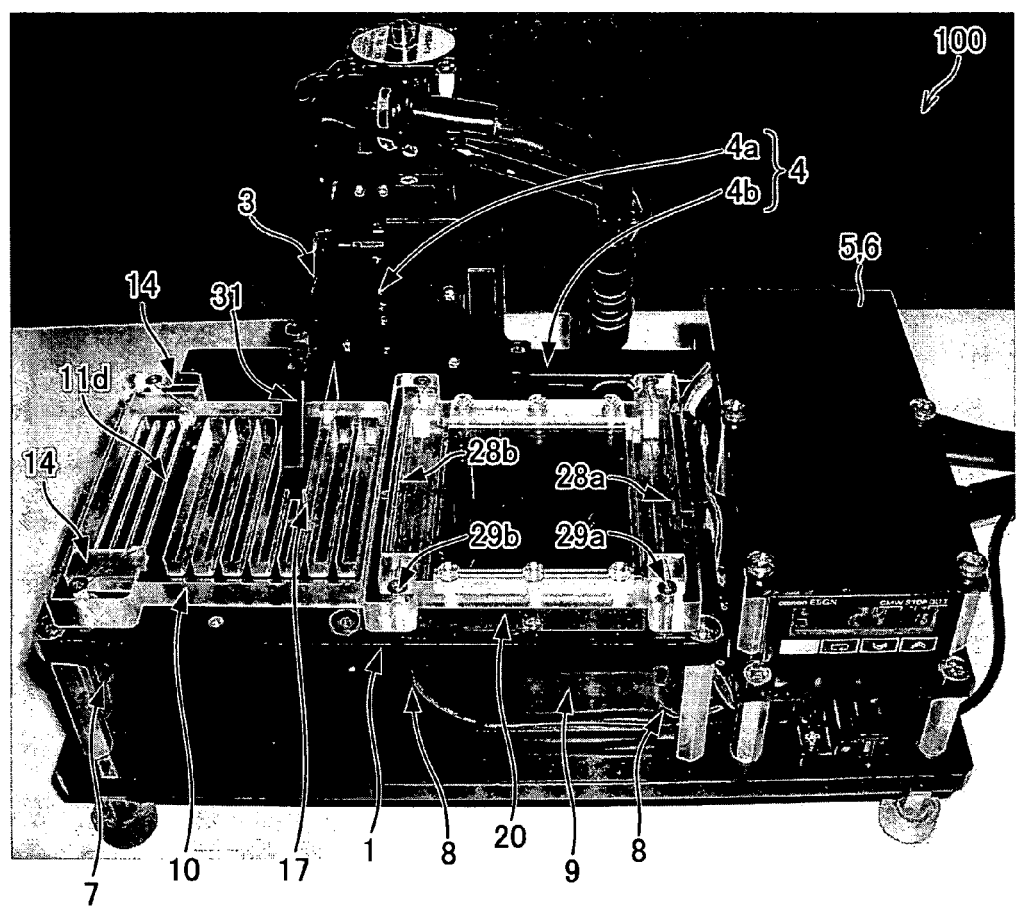
FIG. 9 is a photograph showing an arrangement of the automated two-dimensional electrophoresis apparatus according to one embodiment of the present invention.

As illustrated in FIG. 3, in the automated two-dimensional electrophoresis apparatus 100 according to the present embodiment, the first separation section 10 for performing the first dimensional separation with respect to the sample and the second separation section 20 for performing the second dimensional separation with respect to the sample are fixed on the fixing means 1. The firs separation section 10 includes a plurality of reagent chambers 11 (11a to 11d) and 12 (12a to 12d), and the second separation section 20 includes two chambers (the first buffer solution chamber 28a and the second buffer solution chamber 28b). In FIG. 9, the first separation section 10 includes four reagent chambers 11 and seven reagent chambers 12. However, in order to simplify description of essential parts in FIG. 2 to FIG. 6, the separation section 10 includes four reagent chambers 11 and four reagent chambers 12.

In the first separation section 10, there are performed: the step of introducing the sample into the first medium 15; the step of swelling the first medium 15; the step of applying a voltage to the first medium 15 so as to separate the sample in the first direction; the step of staining the separated sample in the first medium 15; and the step of performing equilibration so as to correspond to the environment of the second separation section 20. The first separation section 10 has a shape suitable for processing the first medium 15 in this manner. The addition of the sample to the first medium 15 and the swelling of the first medium 15 can be separately performed, thereby raising the swelling speed.

The staining step may be performed after separating the sample in the first direction or separating the sample in the second direction as in the conventional art. However, the staining operation is troublesome and requires considerable time, so that it is extremely difficult to automate the staining step. Thus, it is preferable to bind a fluorescent substance to a protein (or DNA) contained in a sample stained after the sample separation in the first direction and before the sample separation in the second direction. Examples of the bond between the fluorescent substance and the protein (or DNA) contained in the sample include covalent bond, ionic bond, coordinate bond, intercalation, and similar bond. However, the bond is not limited to them.

The first separation section 10 is arranged so that grooves (reagent chambers) 11 and 12 are provided in a single insulator. Each of the first reagent chambers 11 stores a reagent required in performing the steps until the first dimensional separation. Each of the second reagent chambers 12 stores a reagent required in after the first dimensional separation and before the second dimensional separation. Specifically, the first reagent chambers 11 are a first medium placement chamber 11a, a sample chamber 11b, a swelling chamber 11c, and a first separation chamber 11d. The sample chamber 11b has a sample introduction section 13. The second reagent chambers 12 are a first equilibration chamber 12a, a staining chamber 12b, a rinsing chamber 12c, and a second equilibration chamber 12d. The first separation chamber 11d is a portion in which the first dimensional separation is performed with respect to the first medium 15, and the first separation chamber 11d is filled with buffer solution required in the first dimensional separation. In case where the reagent to be stored in the swelling chamber 11c contains the buffer solution required in the first dimensional separation, it is not necessary to fill the first separation chamber 11d with the buffer solution required in the first dimensional separation. In the first separation chamber 11d, voltage application performed by the first medium voltage applying means 5 allows the sample contained in the first medium 15 to be separated. It is preferable to provide the first equilibration chamber 12a so as to store buffer solution which displaces the buffer solution used in the separation in the first direction and improves the staining efficiency after performing the separation in the first direction. It is preferable to provide the rinsing chamber 12c so as to store buffer solution for rinsing the first medium 15 to remove an excessive fluorescent pigment adhering to the first medium 15 in the staining chamber 12b which stores the fluorescent pigment. The second equilibration chamber 12d stores a reagent favorable in performing the separation in the second direction, e.g., a reagent for reducing a protein in the first medium 15 and a reagent for performing an SDS process with respect to the protein. Also, buffer solution, surfactant, enzyme, an interacting substance, and a similar substance may be stored in accordance with a method for performing the separation in the second direction.

In the second medium 24, the sample which has been contained in the first medium 15 and has been separated in the first direction is further separated in the second direction different from the first direction. In order to carry out the sample separation in the second direction, in the second separation section 20, there are performed: the step of bringing the first medium 15 containing the sample separated in the first direction into tightly contact with the second medium 24; and the step of applying a voltage to the second medium 24 so as to separate the sample in the second direction. In the automated two-dimensional electrophoresis apparatus 100, also the step of detecting the sample which is being separated in the second direction is performed.

The second separation section 20 includes, at an insulating section 20a obtained by combining the lower insulating plate 21 to the upper insulating plate 22, two grooves (the first buffer solution chamber 28a and the second buffer solution chamber 28b) provided in a lower insulating section so as to penetrate the upper insulating section 22. Further, the lower insulating plate 21 includes a groove (second medium storage section) 24' for covering and storing the second medium 24 between the upper insulating plate 22 and the lower insulating plate 21. The second medium 24 (not shown) stored in the second medium storage section 24' is covered by the insulating section 20a including the lower insulating plate 21 and the upper insulating plate 22, and the second medium 24 can be in contact with outsides of the insulating section 20a at the first opening 25 and the second opening 26.

The first opening 25 and the second opening 26 respectively face the first buffer solution chamber 28a and the buffer solution chamber 28b provided in the second separation section 20. In order to carry out the sample separation in the second direction, the first buffer solution chamber 28a and the buffer solution chamber 28b are respectively filled with the first buffer solution and the second buffer solution via (i) the second medium 24 stored in the second medium storage section 24' and (ii) the first opening 25 and the second opening 26. A first electrode 29a and a second electrode 29b are respectively provided on the first buffer solution chamber 28a and the second buffer solution chamber 28b. When a voltage is applied to the second medium 24 via the first electrode 29a and the second electrode 29b by the second medium voltage applying means 6, a current flows from the first opening 25 to the second opening 26, and the sample is developed/separated from the second opening 26 to the first opening 25.

Figure 8:
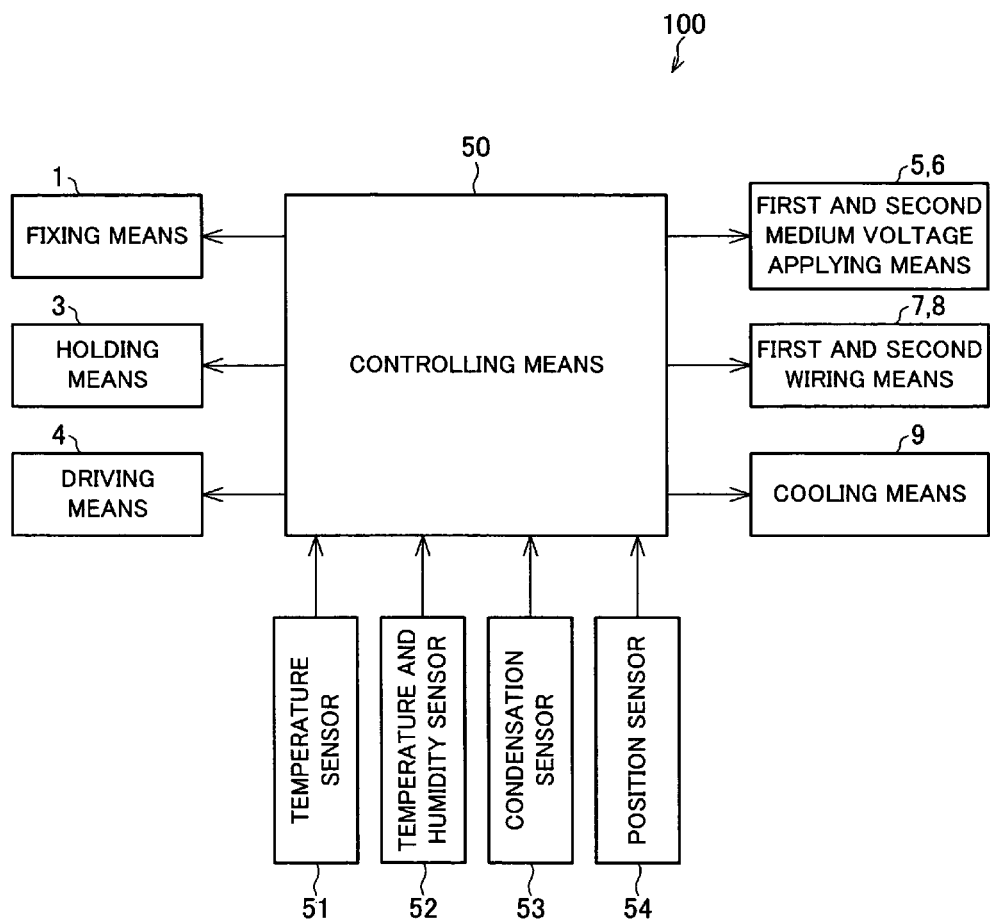
FIG. 8 is a block diagram illustrating a state in which components of the automated two-dimensional electrophoresis apparatus according to one embodiment of the present invention are controlled.

The automated two-dimensional electrophoresis apparatus 100 includes: a buffer member (Δ in FIG. 6) for reducing an external force exerted via the first medium supporter 16; and controlling means 50 for suitably controlling the aforementioned means and for automatically carrying out all the steps after placing in a predetermined position the sample, the reagent, and the separated medium which are required in the two-dimensional electrophoresis. The controlling means 50 receives information from: a temperature sensor (▲ in FIG. 3) for detecting a temperature of the second medium 24 or the buffer solution which is in contact with the second medium 24; a pressure sensor (▲ in FIG. 6) for detecting a direction and/or a strength of an external force exerted via the first medium supporter 16; temperature controlling means for controlling temperatures of the first medium 15 and the second medium 24; a temperature and humidity sensor 52 for detecting a temperature and humidity of the first separation section 10 and/or the second separation section 20 or the vicinity thereof; a condensation sensor 53 for detecting condensation of the first separation section 10 and/or the second separation section 20; a position sensor 54 for detecting a relative position of the fixing means 1 or the holding means 3; and a similar component. Then, in order to realize successful automation, the controlling means 50 outputs control signals for the fixing means 1, the holding means 3 (arm 31), the driving means 4, the first medium voltage applying means 5, the second medium voltage applying means 6, the first wiring means 7, the second wiring means 8, and the cooling means 9 (see FIG. 8). The controlling means of the automated two-dimensional electrophoresis apparatus 100 according to the present embodiment, preferably, can be realized by calculating means such as CPU which is produced by use of various languages and carries out a program code stored in a storage medium such as ROM and/or RAM.

The control begins, so that the driving means 4 moves (carries) the holding means 3. The gel-attached supporter 17 is held by the arm 31 which is a part of the holding means 3, so that the gel-attached supporter 17 on which the first medium 15 is fixed is indirectly moved by the driving means 4 driven by the controlling means and is subjected to a predetermined process as follows.

The gel-attached supporter 17 disposed in the first medium placement chamber 11a is carried to the sample chamber 11b. The gel-attached supporter 17 is kept in the sample chamber 11b until the sample is adsorbed to the first medium 15. A time taken to adsorb the sample is recorded in a storage section of the controlling means. Subsequently, the gel-attached supporter 17 is carried to the swelling chamber 11c and is kept in the swelling chamber 11c until the first medium 15 swells, and is minutely shaken as required. Also information concerning the time and the shaking operation which are required in the swelling of the first medium 15 is recorded in the storage section of the controlling means. The first medium 15 which has swollen on the gel-attached supporter 17 is carried to the first separation chamber 11d, and is disposed between an anode and a cathode of the third electrode 14 in the first separation chamber 11d. At this time, a voltage is applied to the first medium 15 by the first medium voltage applying means 5, so that the sample is separated in the first medium 15 in the first direction. Also information concerning the time and the voltage which are required in performing the sample separation is recorded in the storage section of the controlling means. The aforementioned information is suitably selected and carried out, by a program recorded in the storage section of the controlling means, in accordance with a type of the first medium 15 used therein, a type of the sample, and a type of each reagent.

After finishing the separation in the first medium 15 in the first direction, the first medium 15 is carried to the first equilibration chamber 12a and is minutely shaken as required, thereby performing equilibration so that the subsequent staining operation is favorably performed. Subsequently, the first medium 15 which has been subjected to the equilibration is carried to the staining chamber 12b and is minutely shaken as required, thereby staining the sample contained in the first medium 15. The first medium 15 which has been subjected to the staining is carried to the rinsing chamber 12c and is minutely shaken, thereby suitably removing an excessive pigment. Subsequently, in order to favorably perform the separation in the second medium in the second direction, the first medium 15 which has been subjected to the decoloration is carried to the second equilibration chamber 12d and is minutely shaken as required, thereby performing equilibration so that the subsequent separation in the second medium in the second direction is favorably performed. The first medium 15 which has been subjected to the equilibration is carried to a first medium supplying section 26 of the second medium 24, and is brought into tightly contact with the second medium 24.

After the first medium 15 is brought into tightly contact with the second medium 24, a voltage is applied to the second medium 24 by the second medium voltage applying means 6, so that the sample is separated in the second medium 24 in the second direction. In case of real time monitoring, the monitoring is performed via detection means (not shown) while performing the separation in the second direction. Note that, also information concerning the time and a similar item which are required in the separation at the reagent chambers 12a to 12d and the second medium 24 is recorded in the storage section of the controlling means. The aforementioned information is suitably selected and utilized, by a program recorded in the storage section of the controlling means, in accordance with types of the first medium 15 and the second medium 24 which are used therein, a type of the sample, and a type of each reagent.

In the automated two-dimensional electrophoresis apparatus 100, the controlling means carries out the aforementioned control, so that it is possible to entirely automatically perform the steps of the two-dimensional electrophoresis. Further, the automated two-dimensional electrophoresis apparatus 100 includes the controlling means for carrying out the aforementioned control, so that it is possible to easily select and/or introduce various protocols. As a result, it is possible to improve the sample separation performance. Also, by introducing a two-dimensional high voltage application controlling system in which a computer performs feedback control with respect to a voltage application program of the two-dimensional electrophoresis, it is possible to perform the aforementioned control in combination with the automatic stage.

Note that, the second medium 24 may be produced in the second medium storage section 24'. Alternatively, an additionally prepared second medium 24 may be moved to and fixed in the second medium storage section 24'. In case where the second medium 24 is not produced in the second separation section 20, the second medium storage section 24' does not have to be a groove. In this case, a spacer (not shown) whose size is equal to the thickness of the second medium 24 is disposed so as to surround a portion of the lower insulating plate 21 which portion fixes the second medium 24, and the lower insulating plate 21 and the upper insulating plate 22 are bonded to each other via the spacer.

It is preferable that the second medium 24 is in contact with the buffer solution only at the first opening 25 and the second opening 26, so that the insulator 20a covering the second medium 24 is made of a material having high waterproof property. In order to detect the sample without detaching the second medium 24 from the insulator 20a as in the real time monitoring, it is preferable that the insulator 20a is made of a material having high light transmittance. Examples of the material having both the properties include glass and resin. Examples of the resin material include PMMA, PDMS, COP, polycarbonate, polystyrene, PET, and polyvinyl chloride. In view of the weight, the operability, and the productivity, it is preferable to use acrylic resin (for example, polymethylmethacrylate (PMMA) and a similar component).

In the automated two-dimensional electrophoresis apparatus 100, various steps are carried out while sequentially moving the gel-attached supporter 17. Thus, accuracy in three-dimensionally positioning the gel-attached supporter 17 is important. In this case, it is necessary not only to firmly fix the gel-attached supporter 17 but also to firmly fix the first separation section 10 and the second separation section 20 which relatively move.

The first separation section 10, the second separation section 20, and the gel-attached supporter 17 are replaced for every sample. In consideration for this condition, it is preferable that these components are detachably fixed. Examples of the mechanism fixing the first separation section 10, the second separation section 20, and the gel-attached supporter 17 on the fixing means 1 and the holding means 3 include not only the aforementioned vacuum adsorption mechanism but also a clip fixing mechanism, a magnetic force fixing mechanism, and an electrostatic adsorption mechanism. However, the mechanism is not limited to them. In case of adopting the vacuum adsorption mechanism, it is preferable to fix the foregoing components via a vacuum adsorption plate.

Note that, in case of producing the first separation section 10 and the second separation section 20 by use of transparent PMMA, excitation light is irradiated to a stage (fixing means) 1 below the first separation section 10 and the second separation section 20 in detecting fluorescence of the sample. In case where the stage (fixing means) 1 is bumpy, the excitation light and/or the fluorescent wavelength is unevenly reflected, so that the background rises at the time of detection. This prevents the smooth detection. Thus, it is preferable that: the vacuum adsorption plate has a color tone which allows less reflection; the vacuum adsorption plate is processed so as to have a plane free from any bump; and an adsorption hole for the vacuum adsorption is provided on a portion other than a portion below the detection section of the second separation section 20.

Figure 5:
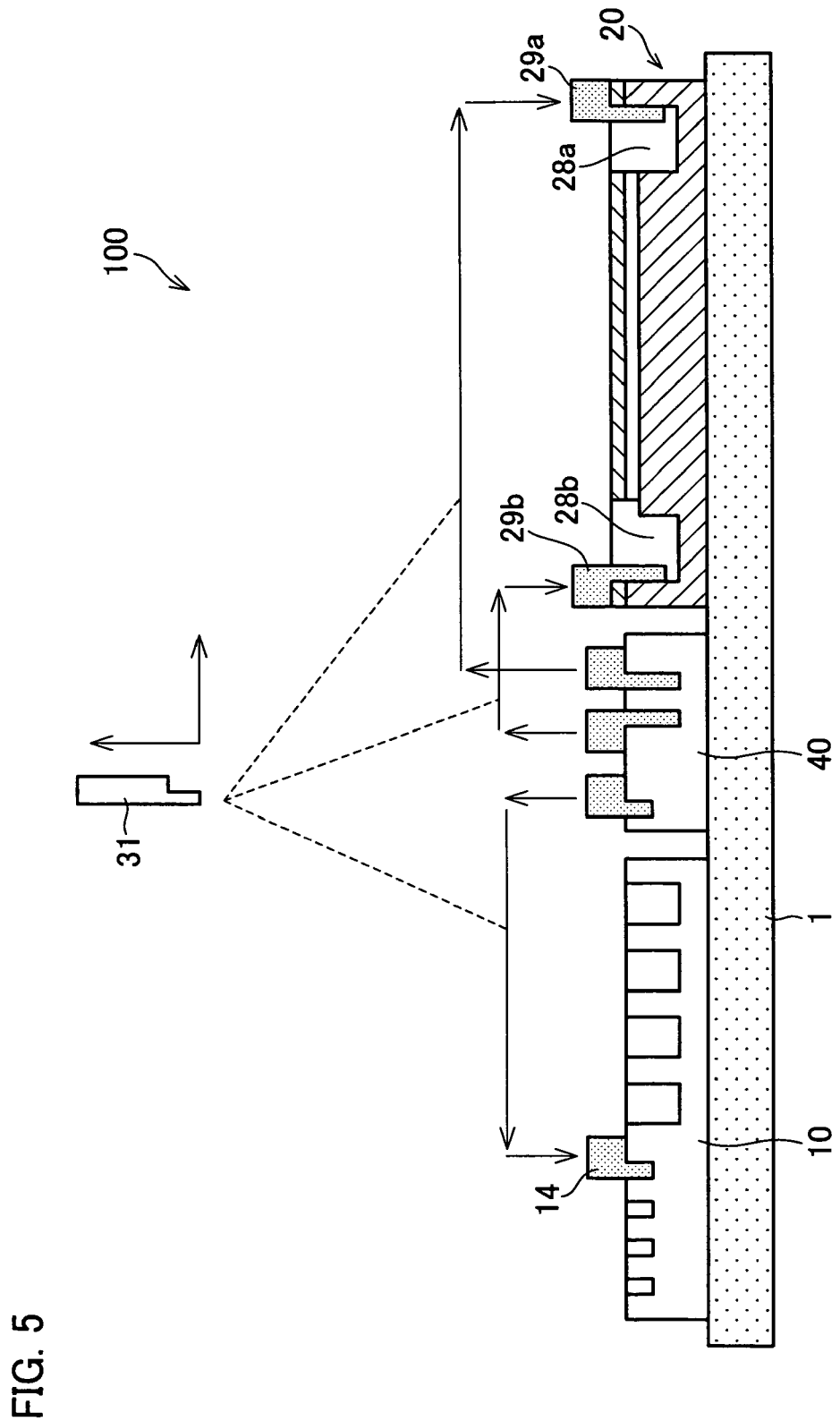
FIG. 5 is a cross sectional view illustrating essential components of the automated two-dimensional electrophoresis apparatus according to one embodiment of the present invention.

The first electrode 29a and the second electrode 29b which are respectively provided on the first buffer solution chamber 28a and the second buffer solution chamber 28b, and the third electrode 14 provided on the first separation section 11d may be fixed or unfixed. In case where these components are fixed, the electrodes 28a, 28b, and 14 may be conductors respectively patterned on the chambers 28a, 28b, and 14. In case of automatically performing carriage/detachment of the electrodes, as illustrated in FIG. 5, the arm 31 carries the electrodes 29a, 29b, and 14 to the chambers 28a, 28b, and 11d respectively so that the electrodes can be attached to/detached from electrode fixing sections (not shown) respectively provided on the chambers. Further, this structure may be arranged so that the electrodes 29a, 29b, and 14 are not fixed on the first buffer solution chamber 28a, the second buffer solution chamber 28b, and the first separation chamber 11d but immersed in buffer solution with which the foregoing chambers are filled. In case of using the electrodes 29a, 29b, and 14 with them capable of being carried, as illustrated in FIG. 5, an electrode rinsing chamber 40 is provided, thereby favorably rinsing the electrodes. Note that, a position in which the electrode rinsing chamber 40 is provided is not limited to a position indicated in FIG. 5 but may be provided in any position of the first separation section 10.

As described above, the first separation section 10 includes a plurality of chambers (reagent chambers) 11 and 12. It is preferable that each of the plural reagent chambers is filled with a reagent required in separating the sample in the first medium 15 and a reagent required in staining the separated first medium 15 (or the sample in the first medium 15), and the reagent to be used can be suitably selected as required. Further, the number of the plural reagent chambers 11 and 12 is increased or decreased according to the required steps.

Figure 6:
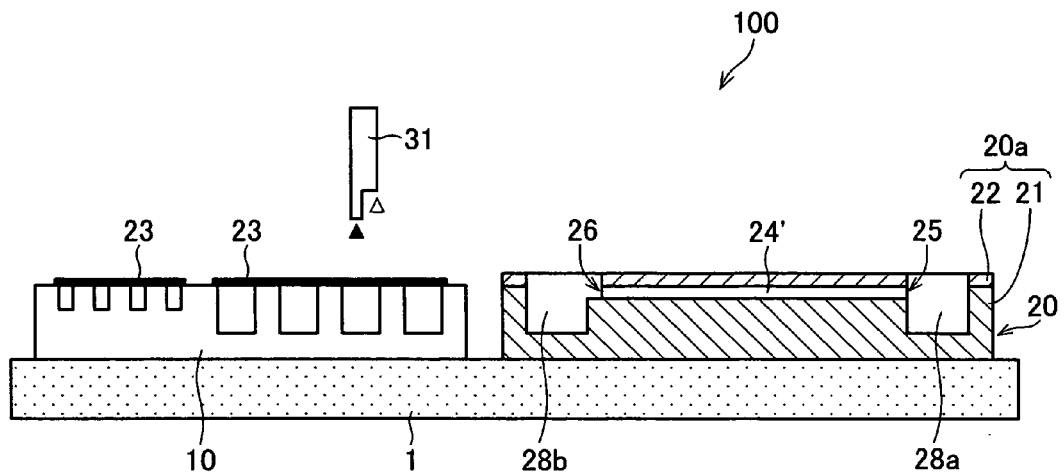
FIG. 6 is a cross sectional view illustrating essential components of the automated two-dimensional electrophoresis apparatus according to one embodiment of the present invention.

In a specific embodiment, each of the plural reagent chambers 11 and 12 includes a sealing sheet which covers the reagent in the chamber and can be removed through peeling (see FIG. 6). By providing the sealing sheet, it is possible to prevent the internally contained reagent from scattering and it is possible to easily reserve the first separation section 10 containing the reagent therein.

In one aspect, the sealing sheet can be removed through peeling by sheet peeling means (not shown) of the automated two-dimensional electrophoresis apparatus 100. It is preferable that the sheet peeling means is driven by the driving means 4. In this case, even when the first separation section 10 is provided on the automated two-dimensional electrophoresis apparatus 100 with the sealing sheet attached to the first separation section 10, the sealing sheet can be favorably removed through peeling under control of the controlling means. Note that, FIG. 6 illustrates a state in which the arm 31 of the holding means 3 serves as the sheet peeling means.

In another aspect, the sealing sheet can be punched by an external force exerted by the gel-attached supporter 17. Further, in order to make it easy to punch the sealing sheet, the first medium supporter 16 may include a punching subsidiary. In this case, it is possible to punch the sealing sheet through ordinary operation of the gel-attached supporter 17 of the first separation section 10 without additionally providing any means such as the sheet peeling means.

In another embodiment, the first separation section 10 includes a preparation-in-use reagent chamber, and the preparation-in-use reagent chamber is a single reagent chamber containing plural reagents with the sealing sheet. When the sealing sheet is removed through peeling or punching, the plural reagents are mixed with each other in the preparation-in-use reagent chamber. In the steps carried out by the automated two-dimensional electrophoresis apparatus 100, even in case of using a reagent which cannot be prepared in advance and requires preparation in use, it is possible to avoid any troublesome operation by using the automated two-dimensional electrophoresis apparatus 100 according to the present embodiment.

The automated two-dimensional electrophoresis apparatus 100 which includes the first separation section 10 having the aforementioned reagent chambers 11 and 12 preferably includes reagent injecting means (not shown) for injecting a reagent into each of the reagent chambers 11 and 12. It is preferable to arrange the reagent injecting means so as to operate in combination with the holding means and the driving means.

In the foregoing description, the present invention was described by explaining, as an example, the case where the insulator 20a, the first buffer solution chamber 28a, and the buffer solution chamber 28b are integrally formed on the second separation section 20. However, these components may be separately formed.

Figure 7:
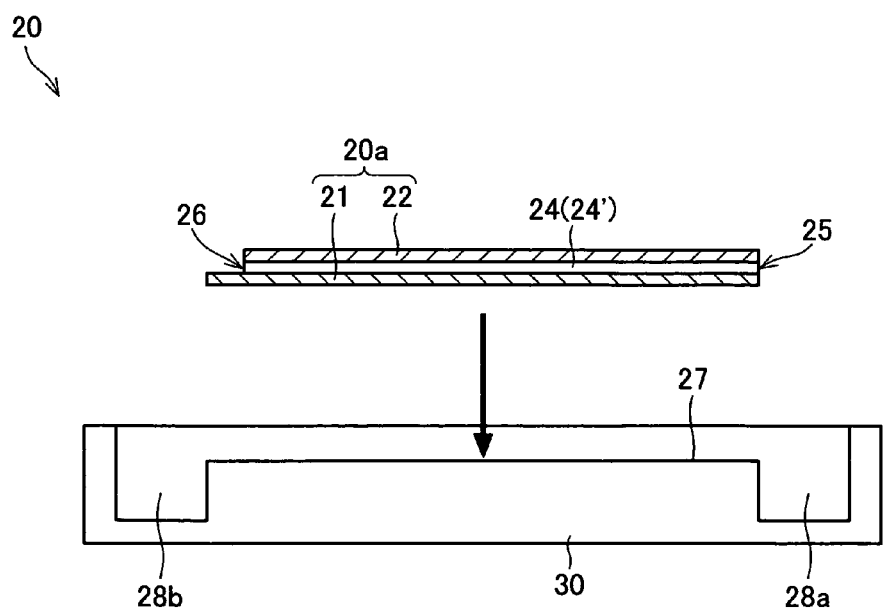
FIG. 7 is a cross sectional view illustrating an arrangement of a sample separation instrument constituting the automated two-dimensional electrophoresis apparatus according to one embodiment of the present invention.

As illustrated in FIG. 7, another embodiment of the second separation section 20 is arranged so as to include: an insulator 20a constituted of a lower insulating plate 21 and an upper insulating plate 22 which sandwich a second medium storage section 24' for storing the second medium 24; an insulator receiving section 27 for receiving the insulator 20a; and a migration chamber 30 having a first buffer solution chamber 28a and a second buffer solution chamber 28b. In the insulator 20a, the lower insulating plate 21 and the upper insulating plate 22 respectively include a first opening 25 and a second opening 26 which respectively allow the second medium 24 to be in contact with buffer solution at the first buffer solution chamber 28a and the second buffer solution chamber 28b. In the migration chamber 30, the insulator receiving section 27 has a plane which can receive the insulator 20a (particularly, the lower insulating plate 21) without any gap therebetween.

In the present embodiment, the insulator 20a and the migration chamber 30 may be constituted of materials identical to each other or materials different from each other. Since the migration chamber 30 is filled with the buffer solution, it is preferable that the migration chamber is made of a material having high waterproof property. It is preferable that the insulator 20a and the migration chamber 30 are fixed. However, it is more preferable that the insulator 20a and the migration chamber 30 are detachable due to a vacuum adsorption mechanism, a clip fixing mechanism, a magnetic force fixing mechanism, or an electrostatic adsorption mechanism. Further, the migration chamber 30 may be arranged so that the insulator receiving section 27, the first buffer solution chamber 28a, and the second buffer solution chamber 28b are separately provided. In this case, any arrangement is possible as long as these components can be in tightly contact with one another so that the buffer solution is supplied to the first opening 25 and the second opening 26 without any leakage. Thus, it is possible to adopt the vacuum adsorption mechanism, the clip fixing mechanism, the magnetic force fixing mechanism, the electrostatic adsorption mechanism, or a similar mechanism.

As described above, the automated two-dimensional electrophoresis apparatus 100 according to the present invention includes: a temperature sensor (▲ in FIG. 3) for detecting a temperature of the second medium or the buffer solution which is in contact with the second medium; a pressure sensor (▲ in FIG. 6) for detecting a direction and/or a strength of an external force exerted via the first medium supporter; temperature controlling means for controlling temperatures of the first medium and the second medium; a temperature and humidity sensor 52 for detecting a temperature and humidity of the first separation section and/or the second separation section or the vicinity thereof; a condensation sensor 53 for detecting condensation of the first separation section and/or the second separation section; a position sensor 54 for detecting a relative position of the fixing means or the holding means; and a similar component. The controlling means 50 receives information from these sensors. Then, in order to realize smooth automation, the controlling means 50 outputs control signals for the fixing means 1, the holding means 3 (arm 31), the driving means 4, the first medium voltage applying means 5, the second medium voltage applying means 6, the first wiring means 7, the second wiring means 8, and the cooling means 9, thereby realizing further advanced automation.

As the temperature sensor, a rhodium, a platinum resistance temperature sensor, a thermistor, and a similar component may be used. It is preferable to dispose the temperature sensor in a place where it is possible to exactly measure temperature of a target whose temperature is to be controlled. An easy process thereof is as follows. A hole is provided in a cooling plate (or the fixing means 1) made of aluminum, copper, or other material having high thermal conductivity, and the temperature sensor is inserted into the hole so as to be fixed (see FIG. 11). Alternatively, the temperature sensor is applied to the cooling plate. Note that, a rhodium is applied to a rear face of the fixing means in FIG. 2. Alternatively, it is possible to use a thermoscope using an infrared ray reflector positioned so as to measure temperature of the whole second separation section 20. Further, for example, an operation for disposing the temperature sensor and an operation for disposing the electrode are simultaneously performed so as to bring the temperature sensor into directly contact with a gel (the first medium 15 or the second medium 24) or migration buffer solution without complicating the operation steps, thereby more exactly monitoring the temperature and more exactly controlling the monitoring. Additionally, a highest heating position in the gel (second medium 24) moves according to a condition under which the electrophoresis is performed particularly in the second dimensional separation, so that it is possible to always keep the entire area of the gel (second medium 24) at constant temperature by respectively controlling temperatures of plural portions obtained by dividing its basic unit in the second direction.

The temperature and humidity sensor is disposed in order to measure a temperature and humidity of an internal space of a housing in which a solution chip (first separation section 10) and a 2D chip (second separation section 20) are disposed. The temperature and humidity sensor may be a combination of a temperature sensor for detecting air temperature of the space and a humidity sensor, or may be a combination of a temperature sensor of the cooling plate and a humidity sensor so as to simplify the arrangement. Alternatively, the humidity condition can be detected by the condensation sensor provided on the cooling plate. The internal space of the apparatus housing in which the solution chip (first separation section 10) and the 2D chip (second separation section 20) are disposed should be closed as tightly as possible by use of an internal cover or the like in order to secure the reproducibility of the separation performance of the apparatus. The arrangement may be made so that a constant temperature and humidity condition is kept and an electrophoresis time and/or an electrophoresis voltage applying program is minutely adjusted in accordance with temperature information or humidity information as required.

In realizing complete automation, the two-dimensional electrophoresis apparatus according to the present invention has various problems. An example of "how to solve the problems" is detailed as follows.

Figure 12:
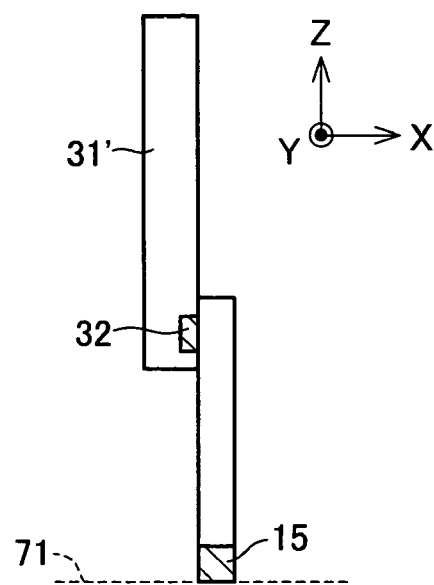
FIG. 12(a) is a schematic illustrating instruments constituting the automated two-dimensional electrophoresis apparatus according to one embodiment of the present invention.
FIG. 12(b) is a schematic illustrating the instruments constituting the automated two-dimensional electrophoresis apparatus according to one embodiment of the present invention.
Figure 12:
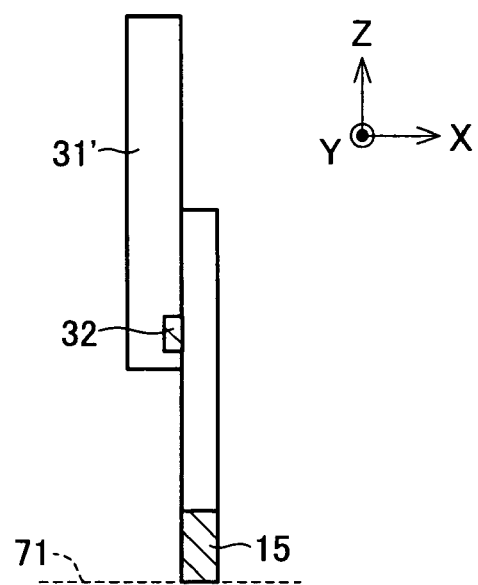

In order that the arm 31 performs the driving in accordance with information (fixing and driving position) written in the program, it is necessary to take the following condition into consideration. That is, in carrying the gel-attached supporter 17 held by the arm 31 to the sample chamber 11b so as to perform the sample introduction, the sample contains a small amount of liquid, so that unevenness in components constituting the apparatus (e.g., the first medium supporter 16, the film provided on the rear face of the first medium 15, the adhesive between the first medium 15 and the first medium supporter 16, and a similar component) and the thickness of the first medium 15 are taken into consideration so that the vertical direction driving means 41 accurately moves the first medium 15 to a bottom of the sample chamber 11b. In this case, it is possible to automatically control the driving position of the arm 31, for example, by using information indicative of whether the first medium 15 reaches the bottom or not in accordance with the pressure sensor without fixing the driving position of the arm 31. A signal indicating the positional information of the bottom of the sample chamber 11b is obtained from the pressure sensor and a feedback operation is performed in accordance with the obtained signal, so that it is possible to carry the first medium 15 to the bottom of the sample chamber 11b, thereby covering the unevenness of the thickness of the gel-attached supporter 17. As to a vertical direction driving position in the subsequent steps, the thickness of the gel-attached supporter 17 can be calculated in accordance with the positional information of the bottom at the time of carriage to the sample chamber 11b, so that the driving is performed in accordance with the information of the thickness of the gel-attached supporter 17. In case of a simpler arrangement in which the pressure sensor is not provided on the two-dimensional electrophoresis apparatus 100, the first medium 15 of the gel-attached supporter 17 is disposed in the first medium placement chamber 11a so as to be in contact with the bottom before beginning the two-dimensional electrophoresis, thereby utilizing the information. That is, the unevenness in the foregoing component (the thickness of the gel-attached supporter 17) is taken into consideration so that a position at which the gel-attached supporter 17 disposed in the first medium placement chamber 11a can be adsorbed is set as the fixing and driving position, thereby covering the unevenness in the foregoing component (the thickness of the gel-attached supporter 17). As a result, it is possible to drive the first medium 15 to the bottom of the sample chamber 11b. Note that, also as to the vertical direction movement in the swelling chamber 11c and subsequent chambers, the automatic control can be performed by using the foregoing method and depth information of each chamber of the first separation section 10 as the fixing and driving position. If the setting is performed in accordance with the adsorption position and the depth information of each chamber, it is possible to cover the unevenness in the foregoing component. The arm 31 and the gel-attached supporter 17 are not tightly adsorbed to each other at a predetermined vertical direction position but are slightly loosely adsorbed to each other. That is, even if the minimum thickness and the maximum thickness of the gel-attached supporter 17 both of which can be varied by the material unevenness have excessively wide ranges, any part of the gel-attached supporter 17 can be adsorbed to the arm (see FIG. 12(a) and FIG. 12(b)).

Further, as the first medium 15 swells in the swelling chamber 11c, a weight (thickness) of the first medium 15 increases with passage of time. The thickness of the swollen first medium 15 can vary depending on a type of the first medium 15 used therein. However, if a time-swelling property is measured in advance according to a type of the first medium 15, it is possible to favorably control the vertical direction according to the swelling time. Alternatively, an amount of swelling liquid with which the swelling chamber is filled is increased in advance, and the vertical direction driving position is set so that a lower end of the swollen gel is positioned above the bottom of the swelling chamber 11c. Only the swelling liquid absorbed by the first medium 15 is carried to the first separation chamber 11d, so that voltage application does not cause a current to excessively flow in the first separation chamber 11d. As a result, the arrangement is free from disadvantage caused by excessively using the swelling liquid. If this technique is adopted, it is possible to favorably cover the unevenness which may occur in the thickness of the swollen first medium 15.

Furthermore, in performing the first direction separation in the first separation chamber 11d, it is necessary to bring the first medium 15 and the third electrode 14 into tightly contact with each other without fail. As described above, there is unevenness in the thickness of the swollen first medium 15. In order to cover the unevenness, a pressure sensor for confirming the contact with the electrode is provided so as to perform feedback control with respect to the vertical direction driving position. In case where the pressure sensor is not used, the gel-attached supporter 17 is carried to the first separation chamber 11d and then is released from the adsorption so as to detach the gel-attached supporter 17 from the arm 31, thereby bringing the first medium 15 which falls due to the gravity into tightly contact with the third electrode 14 without fail. After finishing the first separation, the gel-attached supporter 17 is held by the arm 31 again so as to be used in the subsequent steps. As in the aforementioned example, the arm 31 and the gel-attached supporter 17 are not tightly adsorbed to each other at a predetermined position but are slightly loosely adsorbed to each other. That is, even if a Z position (vertical direction position) of the gel-attached supporter 17 varies before and after performing the first separation, an arm-supporter coupling section 32 in FIG. 12 can be adsorbed to any portion (see FIG. 12(a) and FIG. 12(b)). In the step after the first separation, high accuracy is not required in the vertical direction driving, so that the vertical direction driving position information at the time of the first separation is not essential in the subsequent steps. At this time, it is preferable to use an electromagnetic valve, which causes/stops the vacuum adsorption, in detaching the gel-attached supporter 17 and the arm 31 from each other at the arm-supporter coupling section 32. Alternatively, a minute voltage is applied to the third electrode 14 in advance and the arm holding the gel-attached supporter 17 is lowered under this condition. At this time, it is possible to detect attachment of the first medium 15 and the third electrode 14 by monitoring a current value, so that it is possible to perform feedback control with respect to the vertical direction driving position in accordance with the current value, thereby bringing the first medium 15 and the third electrode 14 into tightly contact with each other without fail. Alternatively, it is possible to lower the arm 31 holding the gel-attached supporter 17 in accordance with the minimum thickness of the first medium 15. In this case, the thickness of the first medium 15 causes the first medium 15 to be strongly pressed against the third electrode 14, but this arrangement seldom raises disadvantage.

Furthermore, in performing the second direction separation in the second medium 24, it is necessary to bring the first medium 15 and the second medium 24 into tightly contact with each other without fail. As described above, the second medium 24 protrudes from the second opening 26, so that both the mediums are in more tightly contact with each other. However, the length of the second medium 24 protruding from the second opening 26 is not necessarily constant. In this case, the second separation section 20 fixed (adsorbed) on the fixing means 1 is temporarily released and the first medium 15 is strongly pressed against the second medium 24, so that it is possible to disperse a force which is not required in attachment of the first medium 15 and the second medium 24 as a force for moving the second separation section 20. Further, the second separation section 20 is fixed (adsorbed) on the fixing means 1 again after the attachment of the first medium 15 and the second medium 24. Note that, it is not necessary to fix the second separation section 20 again. Alternatively, as the arrangement of FIG. 7, it is possible to adopt an arrangement in which the second medium 24 is slidably fixed on the second separation section 20.

In performing the second direction separation in the second medium 24, it is necessary to move the sample contained in the first medium 15 to the second medium 24 without fail. Thus, it is necessary that a vertical direction position of the first medium 15 is identical with a vertical direction position of the second medium 24. There is unevenness in the thickness of the first medium 15, so that the thickness of the second medium 24 is set to be greater than the thickness of the first medium 15, thereby avoiding influence caused by the unevenness in the thickness of the first medium 15.

In order to avoid disadvantages caused by movement of the respective portions due to the driving means 4 (e.g., overflow of buffer solution from the buffer solution chamber, adhesion of solution to a support plate, and a similar disadvantage) or in order to perform the respective steps more quickly, a hydrophilic material or a hydrophobic material is used to constitute each portion.

In case where the two-dimensional electrophoresis apparatus 100 according to the present invention further includes an irradiation section and a detection section, excitation light or fluorescent light is reflected by the arm 31 and/or the gel-attached support plate 17 in detecting the separated sample, so that it may be impossible to favorably perform the detection. In this case, a reflection preventing film is provided on the arm 31 and/or the gel-attached supporter 17, or the arm 31 and/or the gel-attached supporter 17 is made of nonreflecting material.

Figure 13:
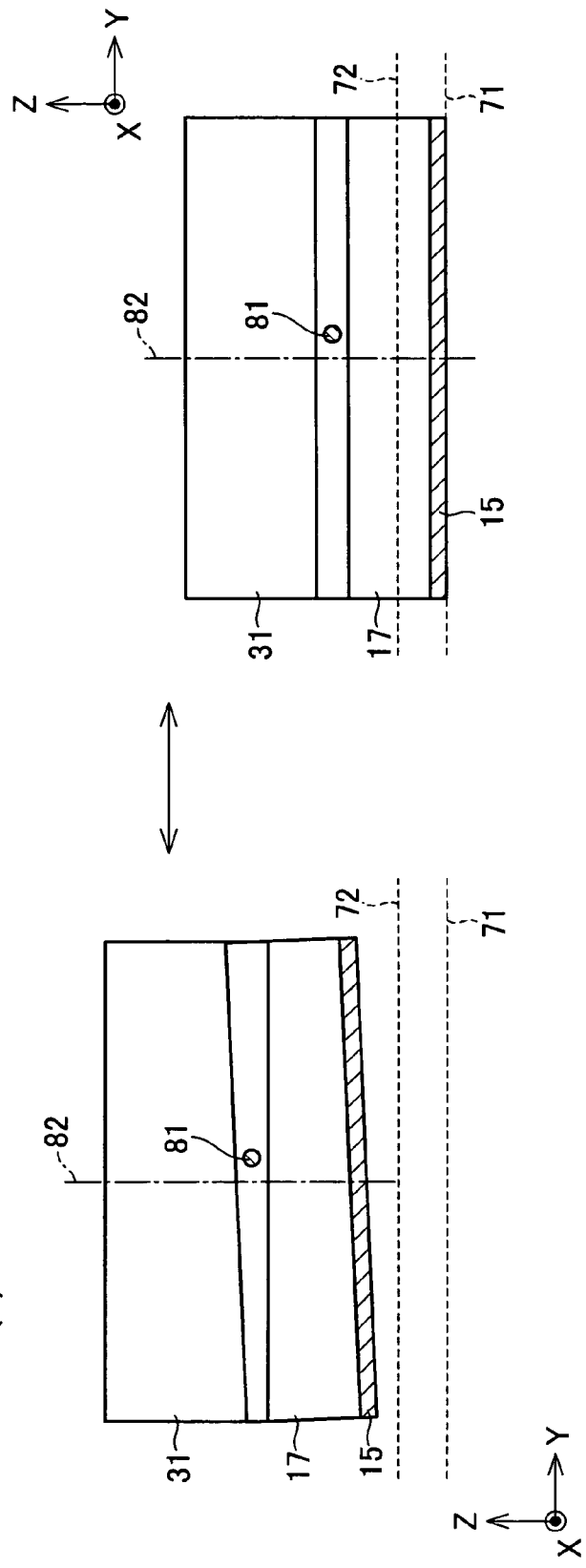
FIG. 13(a) is a schematic illustrating instruments constituting the automated two-dimensional electrophoresis apparatus according to one embodiment of the present invention.
FIG. 13(b) is a schematic illustrating instruments constituting the automated two-dimensional electrophoresis apparatus according to one embodiment of the present invention.

It is necessary to avoid adhesion of air bubbles to the first medium 15 and/or the second medium 24 in order to favorably perform the electrophoresis. However, at the time of movement in the vertical direction, air bubbles are likely to adhere to the first medium 15. In this case, the first medium 15 is provided or kept while a lower face of the first medium 15 is slightly slanted with respect to a horizontal direction. The bottom of the first medium placement chamber 11a is kept slanted at a predetermined angle, so that the arm 31 can hold the gel-attached supporter 17 so that the bottom of the first medium 15 slants with respect to the horizontal face (see FIG. 13(a)). Alternatively, the arm 31 holds a point of the gel-attached supporter 17 so that the point slightly deviates from the gravity point of the gel-attached supporter 17, so that the gel-attached supporter 17 can slightly rotate around a point holding section 81 so that the slight rotation corresponds to the deviation from the gravity point. As a result, the arm 31 can hold the gel-attached supporter 17 so that the bottom of the first medium 15 slants with respect to the horizontal face 72 (see FIG. 13(b) and FIG. 13(c)). It is preferable to arrange the holding section 3 in this case so as to sandwich the point of the gel-attached supporter 17 for fixation or so as to have an axis inserted into a hole provided in the gel-attached supporter 17 for fixation. After the vertical direction driving, it is preferable to perform the fixation so that the undersurface of the first medium 15 is horizontal with respect to the bottom 71 after the first medium 15 reaches each chamber bottom 71. When the first medium 15 reaches the bottom 71, a drag of the bottom 71 causes the slanted first medium 15 to be horizontal (FIG. 13(b)). When the first medium 15 rises in the vertical direction (Z axis), the deviation from the gravity point causes the first medium 15 to be slanted again, so that no air bubble is contained in the subsequent step (FIG. 13(a)). If the vertical direction driving means 41 is operated more slowly, air bubbles are less likely to be contained. If a width of each of the reagent chambers 11 and 12 in the first separation section 20 is made greater than a width of the first medium 15, air bubbles are likely to be released. Further, in attaching the first medium 15 to the second medium 24, if the attachment is made by vertically lowering the first medium 15 from the above of the attachment horizontal position, air bubbles are likely to adhere to the undersurface of the first medium 15 or an interface between the first medium 15 and the second medium 24. It is preferable that: first, the driving means 4 at the time of attachment horizontally drives the arm 31 to a position slightly nearer to the second buffer solution chamber 28b than the attachment horizontal position and then vertically drives the arm 31 in the vertical position at which the second separation is carried out, and lastly the driving means 4 horizontally drives the arm 31 in the attachment horizontal position. Further, the air bubbles adhering to the first medium 15 may be removed by minutely shaking the first medium 15 in a horizontal direction and/or a vertical direction in the second buffer solution chamber 28b before the attachment.

If the solution adhering to the first medium supporter 16 at the time of swelling and/or equilibration drips to the first medium 15, a current value in the first direction separation and/or the second direction separation may be inconstant. Thus, the operation of the vertical direction driving means 41 is favorably controlled so that the solution does not adhere to the first medium supporter 16 at the time of movement in the Z direction. Also, the two-dimensional electrophoresis apparatus 100 according to the present invention may include a mechanism for wiping the solution adhering to the first medium supporter 16 before the gel-attached supporter 17 is carried to the subsequent chamber.

All the professional literatures and all the patent documents which are described in the present specification are hereby incorporated by reference.

EXAMPLE

[First Medium (1D Gel) 15]

As the first medium 15, there was used a dry-type immobilized pH gradient gel which had the thickness of about 0.5 mm at the time of swelling and was cut into a size of about 52 mm×about 1 mm.

Then, a support plate whose size was 52 mm×12 mm ×1 mm was used to fix the first medium 15 thereon so that a fixation area thereof was 52 mm×1 mm. The support plate used was made of glass or resin (for example, PMMA (polymethylmethacrylate)).

[Holding Means (Support Arm) 31]

An adsorption groove whose width was 1 mm and length was 46 mm was formed on the support arm 31 of the holding means 3 for holding the gel-attached supporter 17, and an end of the support plate was adsorbed to the adsorption groove, thereby adsorbing the first medium 15 to the arm. The adsorption was performed or stopped so as to easily attach or detach the first medium 15 to or from the arm and so as to hold and carry an electrophoresis electrode.

[First Separation Section (Solution Chip) 10]

As the first separation section 10, a PMMA substrate A whose size was 70 mm×70 mm×10 mm was used, and a groove having a width of 1.1 mm and a depth of 3 mm, three grooves each of which had a width of 1.5 mm and a depth of 3 mm, and seven grooves each of which had a width of 5 mm and a depth of 9 mm were provided. The gel-attached supporter 17 was stored in the groove having the width of 1.1 mm, and the grooves each of which has the width of 1.5 mm respectively contain or store first medium swelling liquid (electrophoresis buffer solution) and electrodes. The grooves each of which had the width of 5 mm respectively store solution required in the staining step and second equilibration liquid required in the second separation. Further, the gel swollen by introducing the sample was inserted into the groove on which the electrode was disposed, and a voltage was applied by bringing the gel into contact with the electrode, thereby separating the sample in the first direction.

[Second Medium (2D Gel) 24 and Second Separation Section (2D Chip) 20]

As the second separation section 20, a PMMA substrate 21 whose size was 70 mm×70 mm×10 mm was used, and two grooves each of which had a size of 68 mm×9 mm×9 mm were provided in vicinities of both ends of the substrate. Further, in the second separation section 20, a groove (55 mm to 60 mm×0.5 mm to 11.0 mm) whose cross sectional size was equal to or slightly larger than a cross sectional size (52 mm×0.5 mm) of the first medium 15 was provided as the second medium storage section 24'.

Subsequently, the PMMA substrate 22 whose thickness was 5 mm was made overlap the PMMA substrate 21 so that the PMMA substrate 22 partially entered the PMMA substrate 21, and openings were respectively provided in the aforementioned two grooves. Note that, each opening had a size of 68 nm×9 nm.

As illustrated, the second medium 24 was fixed on the substrate 21 and had a portion (its width was about 3 mm) 26 which was not covered by the substrate 22. The two grooves each of which had the size of 68 mm×9 mm respectively constitute (first and second) buffer solution chambers 28a and 28b each of which stores buffer solution. In performing the electrophoresis in the second separation section 20, electrodes were additionally provided on the buffer solution chambers 28a and 28b so as to perform the separation with respect to the sample in the second direction. After fixing the second medium 24 on the substrate 21, the substrate 21 and the substrate 22 were fixed by use of a resin screw or an adhesive.

[Fixing Means (Plate) 1]

Under the first separation section 10 and the second separation section 20, an aluminum cooling and vacuum adsorption plate having been subjected to a black alumite process was provided, and the first separation section 10 and the second separation section 20 were fixed on a single plate 1 by use of a vacuum adsorption mechanism.

[Vacuum Adsorption Mechanism]

As described above, the first separation section 10 and the second separation section 20 each of which had the width of 70 mm were fixed on a single plate by carrying out the vacuum adsorption.

[Driving Means (Automatic Stage) 4]

The driving means 4 for moving and shaking the gel-attached supporter was constituted of an X axis stage and a Z axis stage which were driven by a stepping motor. The driving performance thereof was set to 85 mm for a single stroke (resolution of 1 μm/pulse) in the X axis stage and 15 mm for a single stroke (resolution of 1 μm/pulse) in the Z axis stage, and the driving means 4 was controlled via a general-purpose multiaxial stepping motor controller by using a personal computer connected thereto with a GPIB. Further, the driving means 4 was integrally controlled in combination with other plural devices such as a detection device.

[Cooling Mechanism]

In order to cool the first separation section 10 and the second separation section 20 which were heated by voltage application, two Peltier elements were disposed under the stage 1. Each of the Peltier elements had a capacitance of 51.4 W and a size of 40 mm×40 mm, and its temperature was controlled so as to be a set temperature by a temperature adjuster connected to a K type rhodium serving as a temperature sensor. In the Peltier element, a radiating fin was disposed on the heat radiating side and a cooling DC fan was further disposed on the heat radiating side.

[Voltage Applying Means (Electrophoresis Power Supply) 5 and 6]

As the voltage applying means 5 and 6 for applying voltages respectively to the first medium and the second medium, module type high voltage units each of which can be controlled with a personal computer were used. The voltage applying means 5 and 6 were controlled in line with control of the driving means.

A 10 W high voltage unit whose maximum voltage was 6 kV and maximum current was 1.7 mA was used as the unit for the first medium, and a 30 W high voltage unit whose maximum voltage was 0.6 kV and maximum current was 50 mA was used as the unit for the second medium. Each of the units was controlled by a personal computer on which an AD/DA conversion board was installed. As a result, output voltage setting and a voltage and/or a current were monitored.

[Two-Dimensional Electrophoresis]

The dry type gel-attached supporter 17 was held by the support arm 31 of the holding means 3 by vacuum adsorption, and the driving means 4 moved the holding means 3 in the X direction and the Z direction. Specifically, the first medium 15 was sequentially moved from the first medium chamber 11a through the sample chamber 11b and the swelling chamber 11c to the first separation chamber 11d so as to be inserted into the respective chambers, and the first medium 15 was subjected to a predetermined process. The electrode 14 was disposed so as to cover both ends of the first separation chamber 11d in advance, and the first medium 15 was inserted and held so that both ends of the first medium 15 were in contact with the electrode 14. In accordance with the isoelectric focusing electrophoresis voltage applying program, a voltage was applied to the first medium 15.

After finishing the isoelectric focusing electrophoresis separation, the first medium 15 was sequentially moved and inserted into the reagent chambers of the first equilibration chamber 12a, the staining chamber 12b, the rinsing chamber 12c, and the second equilibration chamber 12d, and the first medium 15 was shaken in each chamber as required. As the shaking operation, repetitive reciprocation with small displacement was performed in the X axis direction and the Z axis direction.

In the second separation section 20, electrophoresis electrodes 29a and 29b were disposed in advance, and the first medium 15 was moved to the second medium 24 and was immersed in the second buffer solution chamber 28b on the anode side, and air bubbles were removed from the surface of the first medium 15 by a shaking operation, and the first medium 15 was tightly pressed against an end face of the second medium 24 at the first medium supplying section 26. Subsequently, a voltage was applied to the second medium 24 in accordance with a second dimensional electrophoresis voltage applying program. The staining was performed before the second dimensional electrophoresis, so that this allowed real time observation of the electrophoresis separation through a CCD camera disposed above the second separation section 20.

In the automated two-dimensional electrophoresis apparatus (FIG. 9) used in the present Example, an operator performed the following steps of:

(i) filling the swelling chamber 11c with gel swelling liquid and filling the second reagent chamber 12 with each reagent;

(ii) applying a sample to a sample introduction section 13 of the sample chamber 11b;

(iii) disposing the gel-attached supporter 17 in the first medium placement chamber 11a;

(iv) disposing the first separation section 10 on the fixing means 1 and tightly fixing the first separation section 10 by vacuum adsorption;

(v) disposing the second separation section 20 on the fixing means 1 and tightly fixing the second separation section 20 by vacuum adsorption;

(vi) disposing the first electrode 29a, the second electrode 29b, and the third electrode 14;

(vii) pushing a start button of the automated two-dimensional electrophoresis apparatus 100;

(viii) removing the first electrode 29a, the second electrode 29b, and the third electrode 14 after finishing all the automation steps of the two-dimensional electrophoresis;

(ix) detaching the first separation section 10 and the second separation section 20 from the fixing means 1; and (x) observing the second separation section 20.

Figure 10:
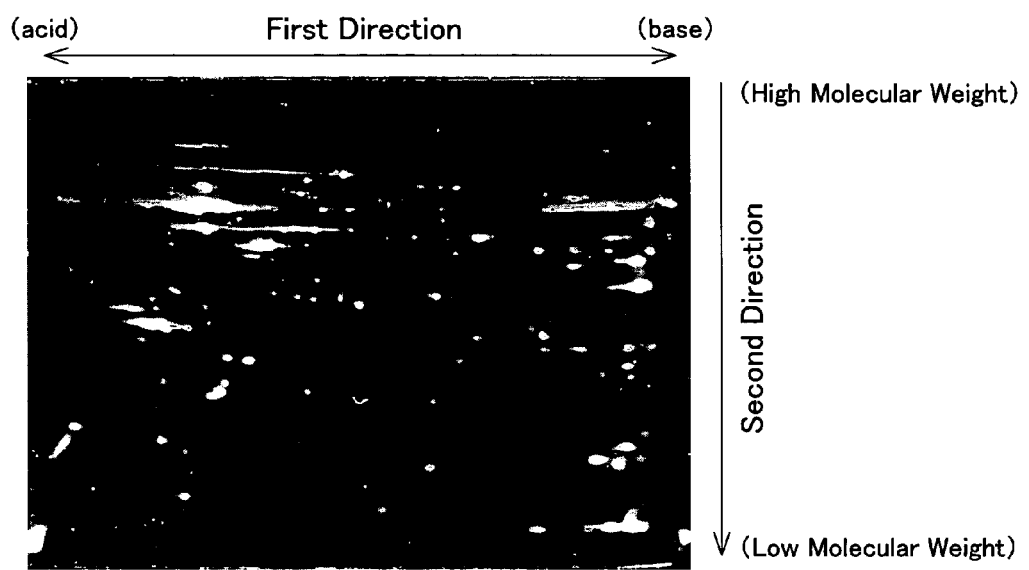
FIG. 10 is a photograph showing a result of separation performed with respect to a mouse cerebral soluble fraction in two-dimensional directions by using the automated two-dimensional electrophoresis apparatus according to one embodiment of the present invention.

By using the automated two-dimensional electrophoresis apparatus according to the present invention whose arrangement other than the foregoing steps (i) to (x) are illustrated in FIG. 9, a mouse cerebral soluble fraction was separated in the two-dimensional directions. FIG. 10 illustrates that the two-dimensional separation of the sample was favorably performed.

In the automated two-dimensional electrophoresis apparatus used in the present Example in the foregoing manner, the operator performs part of all the steps. However, a person skilled in the art who read the present specification will readily understand that it is possible to automate all the steps by suitably setting the program used for the controlling means.

A sample separation instrument according to the present invention includes an insulator for storing a second medium which allows a sample separated in a first medium in a first direction to be further separated in a second direction different from the first direction, wherein: the insulator includes a first opening and a second opening each of which defines the second direction in which the second medium is electrified, and the second opening has a shape which allows the first medium containing the separated sample to be attached to the second medium along the first direction.

The second opening has the foregoing shape, so that the sample separation instrument according to the present invention allows a sample contained in the first medium to favorably move into the second medium. As a result, it is possible to perform the two-dimensional electrophoresis having excellent resolution. Further, if the foregoing arrangement is adopted, the sample separation instrument according to the present invention allows the first medium to be safely in contact with the second medium without stopping application of a high voltage, and then it is possible to remove the first medium as required.

The sample separation instrument according to the present invention may be arranged so that a third opening having a shape which allows the first medium containing the separated sample to be attached to the second medium along the first direction is provided between the first opening and the second opening.

It is preferable to arrange the sample separation instrument according to the present invention so that the insulator includes two insulating plates.

If the foregoing arrangement is adopted, the sample separation instrument according to the present invention can be used in the same manner as in the conventional slabgel.

It is preferable to arrange the sample separation instrument according to the present invention so that the insulator includes two insulating plates and a spacer for defining a thickness of the second medium formed between the insulating plates.

If the foregoing arrangement is adopted, the sample separation instrument according to the present invention can be used in the same manner as in the conventional slabgel.

It is preferable to arrange the sample separation instrument according to the present invention so that the second medium is different from the first medium in a separation parameter.

If the foregoing arrangement is adopted, the sample separation instrument according to the present invention can perform advanced sample separation.

It is preferable to arrange the sample separation instrument according to the present invention so that the insulator stores the second medium.

If the foregoing arrangement is adopted, the sample separation instrument according to the present invention requires no trouble taken to newly prepare a gel.

It is preferable to arrange the sample separation instrument according to the present invention so as to further include: a first buffer solution chamber to be filled with a first buffer solution which is to be in contact with the second medium at the first opening; and a second buffer solution chamber to be filled with a second buffer solution which is to be in contact with the second medium at the second opening.

It is preferable to arrange the sample separation instrument according to the present invention so that the insulator, the first buffer solution chamber, and the second buffer solution chamber are integrally formed.

It is preferable to arrange the sample separation instrument according to the present invention so as to include an insulator receiving section for detachably fixing the insulator thereon so that the insulator receiving section, the first buffer solution chamber, and the second buffer solution chamber are integrally formed.

It is preferable to arrange the sample separation instrument according to the present invention so as to include a first electrode and a second electrode each of which electrifies the second medium so that the first electrode and the second electrode are fixed on the first buffer solution chamber and the second buffer solution chamber respectively.

It is preferable to arrange the sample separation instrument according to the present invention so that the first electrode and the second electrode for electrifying the second medium are made of conductors respectively formed on the first buffer solution chamber and the second buffer solution chamber by patterning.

If the foregoing arrangement is adopted, it is possible to carry out the sample separation more quickly by using the sample separation instrument according to the present invention.

It is preferable to arrange the sample separation instrument according to the present invention so as to further include means for automatically bringing the first medium, in which the sample has been separated in the first direction, into tightly contact with the second opening.

If the foregoing arrangement is adopted, the sample separation instrument according to the present invention allows the first medium and the second medium to be more tightly attached to each other.

A sample separation apparatus according to the present invention includes fixing means, wherein: the fixing means fixes thereon a sample separation instrument having an insulator for storing a second medium which allows a sample separated in a first medium in a first direction to be further separated in a second direction different from the first direction, and the insulator includes a first opening and a second opening each of which defines the second direction in which the second medium is electrified, and the second opening has a shape which allows the first medium containing the separated sample to be attached to the second medium along the first direction.

If the foregoing arrangement is adopted, various steps can be performed more stably in the sample separation apparatus according to the present invention.

It is preferable to arrange the sample separation apparatus according to the present invention the fixing means includes at least one of a vacuum adsorption mechanism, a clip fixing mechanism, a magnetic force fixing mechanism, and an electrostatic adsorption mechanism.

If the foregoing arrangement is adopted, the sample separation instrument can be detachably fixed on the sample separation apparatus according to the present invention.

It is preferable to arrange the sample separation apparatus according to the present invention so as to further include: holding means for holding a first medium supporter which supports the first medium; and driving means for moving the fixing means or the holding means in a direction parallel or perpendicular to a plane whose sides extend in the first direction and in the second direction.

If the foregoing arrangement is adopted, the processing steps can be automated in the sample separation apparatus according to the present invention.

It is preferable to arrange the sample separation apparatus according to the present invention so as to further include second medium voltage applying means for applying a voltage to the second medium.

It is preferable to arrange the sample separation apparatus according to the present invention so as to include second wiring means for connecting the first electrode and the second electrode to the second medium voltage applying means.

It is preferable to arrange the sample separation apparatus according to the present invention so that: the holding means holds the first electrode and the second electrode, and the driving means disposes the first electrode and the second electrode in the first buffer solution chamber and the second buffer solution chamber respectively.

If the foregoing arrangement is adopted, the processing steps and the step of replacing and/or rinsing the electrode can be automated in the sample separation apparatus according to the present invention.

It is preferable to arrange the sample separation apparatus according to the present invention so that a first direction separation instrument for separating the sample in the first medium in the first direction is further fixed.

It is preferable to arrange the sample separation apparatus according to the present invention so that the first direction separation instrument includes a first separation chamber for performing first separation.

If the foregoing arrangement is adopted, the two-dimensional electrophoresis can be carried out in the sample separation apparatus according to the present invention.

It is preferable to arrange the sample separation apparatus according to the present invention so that the third electrode for electrifying the first medium is fixed on the first separation chamber.

It is preferable to arrange the sample separation apparatus according to the present invention so that the third electrode is made of a conductor formed on the first separation chamber by patterning.

If the foregoing arrangement is adopted, the electrode can be provided at the same time as in producing the first direction separation instrument.

It is preferable to arrange the sample separation apparatus according to the present invention so as to further include first medium voltage applying means for applying a voltage to the first medium.

It is preferable to arrange the sample separation apparatus according to the present invention so as to include first wiring means for connecting the third electrode to the first medium voltage applying means.

It is preferable to arrange the sample separation apparatus according to the present invention so that the third electrode is held by the holding means and is disposed in the first separation chamber by the driving means.

If the foregoing arrangement is adopted, it is possible to automate the processing steps in the sample separation apparatus according to the present invention, so that it is possible to easily replace and/or rinse the electrode of the sample separation apparatus according to the present invention.

It is preferable to arrange the sample separation apparatus according to the present invention so that the first direction separation instrument further includes a plurality of reagent chambers.

It is preferable to arrange the sample separation apparatus according to the present invention so that a sealing sheet for sealing each reagent chamber filled with a reagent is provided.

It is preferable to arrange the sample separation apparatus according to the present invention so that sheet peeling means for peeling the sealing sheet or sheet punching means for punching the sealing sheet is provided on the holding means.

It is preferable to arrange the sample separation apparatus according to the present invention so that the sealing sheet is capable of being punched by an extrusive external force of a first dimensional separation medium supporter held by the holding means.

It is preferable to arrange the sample separation apparatus according to the present invention so that the reagent chambers are partially or respectively filled with a plurality of reagents which are covered by the sealing sheet and which are separated from each other by the sealing sheet, and the plurality of reagents are mixed with each other by peeling or punching the sealing sheet.

It is preferable to arrange the sample separation apparatus according to the present invention so as to further include reagent injecting means for injecting the reagent into the reagent chamber.

It is preferable to arrange the sample separation apparatus according to the present invention so as to include cooling means for cooling the fixing means.

It is preferable to arrange the sample separation apparatus according to the present invention so as to further include temperature controlling means for controlling temperatures of the first medium and the second medium.

It is preferable to arrange the sample separation apparatus according to the present invention so that the temperature controlling means includes a temperature sensor for detecting a temperature of the second medium or a buffer solution which is in contact with the second medium.

It is preferable to arrange the sample separation apparatus according to the present invention so that the holding means holds the first medium supporter.

It is preferable to arrange the sample separation apparatus according to the present invention so that the holding means includes a pressure sensor for detecting a direction and/or a strength of an external force exerted via the first medium supporter.

It is preferable to arrange the sample separation apparatus according to the present invention so that the holding means includes a buffer member for reducing an external force exerted via the first medium supporter.

It is preferable to arrange the sample separation apparatus according to the present invention so as to further include automatic carrying means for carrying the first direction separation instrument and/or the sample separation instrument from an outside of the fixing means so as to set the first direction separation instrument and/or the sample separation instrument in a fixation position of the fixing means.

It is preferable to arrange the sample separation apparatus according to the present invention so as to further include automatic carrying means for carrying the first direction separation instrument and/or the sample separation instrument from the fixation position of the fixing means to an outside of the fixing means.

It is preferable to arrange the sample separation apparatus according to the present invention so as to include a temperature and humidity sensor for detecting a temperature and humidity of the first direction separation instrument and/or the sample separation instrument or a temperature and humidity in a vicinity of the first direction separation instrument and/or the sample separation instrument.

It is preferable to arrange the sample separation apparatus according to the present invention so as to include a condensation sensor for detecting condensation of the first direction separation instrument and/or the sample separation instrument.

It is preferable to arrange the sample separation apparatus according to the present invention so as to further include controlling means for synchronously controlling the fixing means, the holding means, the driving means, the first medium voltage applying means, and the second medium voltage applying means.

If the foregoing arrangement is adopted, it is possible to carry out the sample separation more quickly by using the sample separation instrument according to the present invention.

It is preferable to arrange the sample separation apparatus according to the present invention so that at least one of the fixing means, the holding means, and the driving means includes a position sensor for detecting a relative position of the fixing means or the holding means.

An automated two-dimensional electrophoresis apparatus according to the present invention includes:

holding means for holding a first medium supporter which supports a first medium;

fixing means for fixing thereon a first separation section and a second separation section which supports a second medium;

driving means for moving a relative positional relation of the holding means and the fixing means substantially in a horizontal direction and substantially in a vertical direction;

first medium voltage applying means for applying a voltage to the first medium; and second medium voltage applying means for applying a voltage to the second medium.

It is preferable to arrange the two-dimensional electrophoresis apparatus according to the present invention so that each of the first medium and the second medium is a separation gel.

It is preferable to arrange the two-dimensional electrophoresis apparatus according to the present invention so that the holding means or the fixing means includes at least one of a vacuum adsorption mechanism, a clip fixing mechanism, a magnetic force fixing mechanism, and an electrostatic adsorption mechanism.

It is preferable to arrange the two-dimensional electrophoresis apparatus according to the present invention so that the driving means is biaxial driving means.

It is preferable to arrange the two-dimensional electrophoresis apparatus according to the present invention so that the first medium supporter is held by the holding means.

It is preferable to arrange the two-dimensional electrophoresis apparatus according to the present invention so that the holding means includes a pressure sensor for detecting a direction and/or a strength of an external force exerted via the first medium supporter.

It is preferable to arrange the two-dimensional electrophoresis apparatus according to the present invention so that the first medium supporter is an insulator having a substantially plate shape, and the first medium is formed on an end face of the insulator.

It is preferable to arrange the two-dimensional electrophoresis apparatus according to the present invention so that the first separation section and the second separation section are fixed on the fixing means.

It is preferable to arrange the two-dimensional electrophoresis apparatus according to the present invention so that the first separation section includes one or more first reagent chambers and one or more second reagent chambers.

It is preferable to arrange the two-dimensional electrophoresis apparatus according to the present invention so as to further include droplet expanding means for defining a range in which the reagent provided in each of the first reagent chamber and the second reagent chamber is expanded.

It is preferable to arrange the two-dimensional electrophoresis apparatus according to the present invention so that each of the first reagent chamber and the second reagent chamber is coated so as to define an angle at which the reagent provided in each of the first reagent chamber and the second reagent chamber is in contact with each of the first reagent chamber and the second reagent chamber.

It is preferable to arrange the two-dimensional electrophoresis apparatus according to the present invention so that a third electrode is provided on one of the first reagent chambers.

It is preferable to arrange the two-dimensional electrophoresis apparatus according to the present invention so that the third electrode includes a film-shaped conductor formed on a part of the first separation section by patterning.

It is preferable to arrange the two-dimensional electrophoresis apparatus according to the present invention so as to further include first wiring means which is formed so as to integrally operate with the holding means and allows the first medium voltage applying means and the third electrode to be connected to each other.

It is preferable to arrange the two-dimensional electrophoresis apparatus according to the present invention so that there is provided a sealing sheet which is removable through peeling and seals the first separation section filled with the reagent.

It is preferable to arrange the two-dimensional electrophoresis apparatus according to the present invention so as to further include sheet peeling means for peeling the sealing sheet.

It is preferable to arrange the two-dimensional electrophoresis apparatus according to the present invention so that the sheet peeling means is driven by the driving means.

It is preferable to arrange the two-dimensional electrophoresis apparatus according to the present invention so that the sealing sheet is capable of being punched by an extrusive external force of the first medium supporter held by the holding means.

It is preferable to arrange the two-dimensional electrophoresis apparatus according to the present invention so that one of the first reagent chamber and the second reagent chamber serves as an in-use-preparation reagent chamber filled with a plurality of reagents which are covered by the sealing sheet and which are separated from each other by the sealing sheet, and the plurality of reagents are mixed with each other by peeling or punching the sealing sheet.

It is preferable to arrange the two-dimensional electrophoresis apparatus according to the present invention so as to further include reagent injecting means for injecting the reagent into each of the first reagent chamber and the second reagent chamber.

It is preferable to arrange the two-dimensional electrophoresis apparatus according to the present invention so that the second separation section includes an area where the second medium is formed and areas (a first buffer solution chamber and a second buffer solution chamber) each of which is filled with an electrophoresis buffer solution reagent, and a material different from a material of the second separation section is provided on the area where the second medium is formed.

It is preferable to arrange the two-dimensional electrophoresis apparatus according to the present invention so that an end face of at least one side of the second medium protrudes from an end face of the second separation section which end face is positioned in a direction of a top face of the second medium.

It is preferable to arrange the two-dimensional electrophoresis apparatus according to the present invention so that there is provided a sealing sheet which is removable through peeling and seals the second separation section filled with the medium or the reagent.

It is preferable to arrange the two-dimensional electrophoresis apparatus according to the present invention so that each of the first electrode and the second electrode includes a conductor formed on a part of the second separation section by patterning.

It is preferable to arrange the two-dimensional electrophoresis apparatus according to the present invention so as to further include second wiring means which is formed so as to integrally operate with the holding means and connects the second medium voltage applying means to the first electrode and the second electrode.

It is preferable to arrange the two-dimensional electrophoresis apparatus according to the present invention so as to further include automatic vessel replacing means which supplies and carries the first separation section or the second separation section from a vessel carrier, disposed in an outside of the fixing means, to a fixation position of the fixing means.

It is preferable to arrange the two-dimensional electrophoresis apparatus according to the present invention so that the first separation section and the second separation section are integrally formed.

It is preferable to arrange the two-dimensional electrophoresis apparatus according to the present invention so as to further include temperature controlling means for controlling a temperature of the first medium or the second medium.

It is preferable to arrange the two-dimensional electrophoresis apparatus according to the present invention so that a temperature control setting program for carrying out the temperature controlling means is executed in accordance with an applied voltage setting program for carrying out the first medium voltage applying means or the second medium voltage applying means.

It is preferable to arrange the two-dimensional electrophoresis apparatus according to the present invention so that the temperature controlling means further includes a temperature sensor for detecting a temperature of the second medium or the electrophoresis buffer solution reagent in the second separation section.

It is preferable to arrange the two-dimensional electrophoresis apparatus according to the present invention so that the temperature controlling means includes a plurality of temperature controlling areas.

It is preferable to arrange the two-dimensional electrophoresis apparatus according to the present invention so as to include a temperature and humidity sensor for detecting a temperature and humidity of in a vicinity of the first separation section or the second separation section.

It is preferable to arrange the two-dimensional electrophoresis apparatus according to the present invention so as to include a condensation sensor for detecting condensation of the first separation section or the second separation section.

It is preferable to arrange the two-dimensional electrophoresis apparatus according to the present invention so that the first medium includes a phospholipid.

It is preferable to arrange the two-dimensional electrophoresis apparatus according to the present invention so that the second medium includes a phospholipid.

It is preferable to arrange the two-dimensional electrophoresis apparatus according to the present invention so as to further include:

a third electrode which is held by the holding means and is moved by the driving means so as to be disposed in the first separation chamber; and a first electrode and a second electrode which are held by the holding means and are moved by the driving means so as to be disposed in a predetermined position of the second separation section.

It is preferable to arrange the two-dimensional electrophoresis apparatus according to the present invention so as to further include controlling means for controlling the holding means, the fixing means, the driving means, the first medium voltage applying means, and the second medium voltage applying means.

It is preferable to arrange the two-dimensional electrophoresis apparatus according to the present invention so that at least one of the holding means, the fixing means, and the driving means includes a position sensor for detecting a relative position with respect to the first separation section or the second separation section.

It is preferable to arrange the two-dimensional electrophoresis apparatus according to the present invention so as to include: a sample introducer formed on a part of the first medium supporter so as to sandwich an area dividing slit; and the first separation section in which another reagent chamber is formed on an area corresponding to an area width of the sample introducer.

It is preferable to arrange the two-dimensional electrophoresis apparatus according to the present invention so that the reagent provided in each of the first reagent chamber and the second reagent chamber is a second dimensional separation marker.

It is preferable to arrange the two-dimensional electrophoresis apparatus according to the present invention so that the sample introducer is another first medium.

It is preferable to arrange the two-dimensional electrophoresis apparatus according to the present invention so that the second dimensional separation marker has a capsule shape.

It is preferable to arrange the two-dimensional electrophoresis apparatus according to the present invention so that at least one of the first medium supporter, the first separation section, and the second separation section includes identifying means.

It is preferable to arrange the two-dimensional electrophoresis apparatus according to the present invention so that the identifying means is an IC tag.

It is preferable to arrange the two-dimensional electrophoresis apparatus according to the present invention so that the identifying means is a bar code.

A two-dimensional electrophoresis method according to the present invention includes:

a supporter holding step in which holding means is made to hold a first medium supporter;

a sample introducing step in which a first medium is introduced into a first reagent chamber filled with an electrophoresis sample and a separated medium swelling liquid;

a first dimensional electrophoresis step in which a first medium is inserted into the first separation chamber and first medium voltage applying means is made to apply a voltage;

a reagent processing step in which the first medium is sequentially inserted into a second reagent chamber filled with a plurality of reagent; and a second dimensional electrophoresis step in which the first medium is connected to the second medium and second medium voltage applying means is made to apply a voltage.

It is preferable to arrange the two-dimensional electrophoresis method according to the present invention so that the sample introducing step includes a swelling promotion step based on a minute shaking operation performed with respect to the first medium.

It is preferable to arrange the two-dimensional electrophoresis method according to the present invention so that the minute shaking operation is performed by applying a supersonic wave.

It is preferable to arrange the two-dimensional electrophoresis method according to the present invention so that the sample introducing step includes a swelling promotion step based on temperature control performed with respect to the first medium.

It is preferable to arrange the two-dimensional electrophoresis method according to the present invention so that the reagent processing step includes a shaking operation step based on minute displacement reciprocation of the driving means in a horizontal direction and/or a vertical direction with the first medium immersed in the first reagent chamber and the second reagent chamber.

It is preferable to arrange the two-dimensional electrophoresis method according to the present invention so that the reagent processing step includes a liquid removing step.

It is preferable to arrange the two-dimensional electrophoresis method according to the present invention so that the liquid removing step is performed by using a filter paper.

It is preferable to arrange the two-dimensional electrophoresis method according to the present invention so that the reagent processing step includes:

a staining step in which the first medium is immersed into a staining chamber so as to stain an electrophoresis sample in the first medium;

a pigment removing step in which the first medium is immersed into a rinsing chamber so as to remove a pigment, having not stained the sample, through rinse; and an equilibrating step in which the first medium is immersed into a second equilibration chamber so as to equilibrate the electrophoresis sample.

It is preferable to arrange the two-dimensional electrophoresis method according to the present invention so that the reagent processing step includes a high viscosity providing step in which the first medium is immersed into a high viscosity chamber after the equilibration so as to provide high viscosity liquid around the first medium.

It is preferable to arrange the two-dimensional electrophoresis method according to the present invention so as to includes, after the staining step and before the second dimensional electrophoresis step, a pigment migration removing step in which migration removal of a pigment having not stained the sample is performed by immersing the first medium into an electrophoresis buffer solution reagent chamber and the voltage applying means is made to apply a voltage.

It is preferable to arrange the two-dimensional electrophoresis method according to the present invention so that a direction in which the voltage is applied in the pigment migration removing step is positively or negatively inverted during the voltage application.

It is preferable to arrange the two-dimensional electrophoresis method according to the present invention so that the electrophoresis buffer solution reagent chamber used in the pigment migration removing step is the second buffer solution chamber provided in the second separation section, and the voltage applying means is the second medium voltage applying means.

It is preferable to arrange the two-dimensional electrophoresis method according to the present invention so that the pigment migration removing step is performed before the equilibrating step.

It is preferable to arrange the two-dimensional electrophoresis method according to the present invention so that the first medium is connected to the second medium while the second medium voltage applying means is applying the voltage in the second dimensional electrophoresis step.

It is preferable to arrange the two-dimensional electrophoresis method according to the present invention so that the first medium is removed from the second medium while the second medium voltage applying means is applying the voltage in the second dimensional electrophoresis step.

It is preferable to arrange the two-dimensional electrophoresis method according to the present invention so as to include:

a third electrode shaking rinse step in which driving means is made to perform minute displacement reciprocation of a third electrode, held by holding means and moved by driving means, in a horizontal direction and/or a vertical direction with the third electrode immersed in an electrode rinsing section; and a first electrode and second electrode shaking rinse operation step in which the driving means is made to perform minute displacement reciprocation of a second dimensional electrophoresis apparatus, held by holding means and moved by driving means, in a horizontal direction and/or a vertical direction with the second dimensional electrophoresis apparatus immersed in the electrode rinsing section.

If the present invention is adopted, merely by setting and operating a plurality of chips (migration chambers) in beginning the process, it is possible to automatically perform all the steps of two-dimensional electrophoresis and it is possible to easily select and/or introduce various protocols in improving the separation performance. Further, according to the arrangement of the present invention, it is possible to provide members constituting the present invention as disposable members.

The present invention which can solve disadvantages of a two-dimensional electrophoresis apparatus allows further advancement of proteomics which has been widely practiced. As a result, it is possible to activate the market by separately producing and selling the automated two-dimensional electrophoresis apparatus of the present invention and various members used therein.

The embodiments and concrete examples of implementation discussed in the foregoing detailed explanation serve solely to illustrate the technical details of the present invention, which should not be narrowly interpreted within the limits of such embodiments and concrete examples, but rather may be applied in many variations within the spirit of the present invention, provided such variations do not exceed the scope of the patent claims set forth below.

What is claimed is:

1. A sample separation instrument, comprising:
    a fixing means comprising;
    an insulator for storing a second medium which allows a sample separated in a first medium in a first direction to be further separated in a second direction different from said first direction,
    said insulator comprising a first opening and a second opening each of which defines the second direction in which said second medium is electrified,
    a first medium supporter which is an insulator having a substantially plate shape, and
    a means for automatically bringing said first medium, in which said sample has been separated in said first direction, into tight contact with said second opening by moving said first medium in a direction parallel or perpendicular to said fixing means whose sides extend in said first direction and in said second direction,
    wherein said second opening has a shape which allows said first medium containing the separated sample to be attached to said second medium along said first direction,
    wherein said first medium is fixed on an end face of said first medium supporter and said means for automatically bringing said first medium into tight contact with said second medium holds said first medium supporter such that said first medium faces downward.

2. The sample separation instrument as set forth in claim 1, wherein a third opening having a shape which allows the first medium containing the separated sample to be attached to the second medium along the first direction is provided between the first opening and the second opening.

3. The sample separation instrument as set forth in claim 1, wherein the insulator includes two insulating plates.

4. The sample separation instrument as set forth in claim 1, wherein the second medium is different from the first medium in a separation parameter.

5. The sample separation instrument as set forth in claim 1, further comprising:
    a first buffer solution chamber to be filled with a first buffer solution which is to be in contact with the second medium at the first opening; and a second buffer solution chamber to be filled with a second buffer solution which is to be in contact with the second medium at the second opening.

6. The sample separation instrument as set forth in claim 5, wherein the insulator, the first buffer solution chamber, and the second buffer solution chamber are integrally formed.

7. The sample separation instrument as set forth in claim 5, further comprising an insulator receiving section for detachably fixing the insulator thereon so that the insulator receiving section, the first buffer solution chamber, and the second buffer solution chamber are integrally formed.

8. The sample separation instrument as set forth in claim 5, further comprising a first electrode and a second electrode each of which electrifies the second medium so that the first electrode and the second electrode are fixed on the first buffer solution chamber and the second buffer solution chamber respectively.

9. The sample separation instrument as set forth in claim 1, wherein the second medium protrudes from the second opening.

10. A sample separation apparatus, comprising:
a fixing means, wherein:
said fixing means fixes thereon a sample separation instrument having an insulator for storing a second medium which allows a sample separated in a first medium in a first direction to be further separated in a second direction different from said first direction,
said insulator comprises a first opening and a second opening each of which defines said second direction in which said second medium is electrified; and
said second opening has a shape which allows said first medium containing said separated sample to be attached to said second medium along said first direction; and
a first medium supporter, which is an insulator having a substantially plate shape wherein said first medium is fixed on an end face of said first medium supporter;
a holding means, which is a support arm for holding said first medium supporter;
a driving means, which is an automatic stage for moving said support arm or said fixing means in a direction parallel or perpendicular to a plane whose sides extend in said first direction and in said second direction; and
a means for automatically bringing said first medium, in which said sample has been separated in said first direction, into tight contact with said second opening wherein said means for automatically bringing said first medium into tight contact with said second medium holds said first medium supporter such that said first medium faces downward.

11. The sample separation apparatus as set forth in claim 10, wherein the fixing means includes at least one of a vacuum adsorption mechanism, a clip fixing mechanism, a magnetic force fixing mechanism, and an electrostatic adsorption mechanism.

12. The sample separation apparatus as set forth in claim 10, further comprising a cooling means for cooling the fixing means.

13. The sample separation apparatus as set forth in claim 10, wherein the holding means includes a pressure sensor for detecting a direction and/or a strength of an external force exerted via the first medium supporter.

14. The sample separation apparatus as set forth in claim 10, wherein the holding means includes a buffer member for reducing an external force exerted via the first medium supporter.

15. The sample separation apparatus as set forth in claim 10, wherein the second medium protrudes from the second opening.

16. The sample separation apparatus as set forth in claim 10, wherein the holding means is vacuum adsorption means.

17. The sample separation apparatus as set forth in claim 10, wherein the first medium comprises a lower surface that slants in a horizontal direction.

18. The sample separation apparatus as set forth in claim 10, further comprising a first medium voltage applying means for applying a voltage to the first medium and a second medium voltage applying means for applying a voltage to the second medium.

19. The sample separation apparatus as set forth in claim 18, further comprising controlling means for synchronously controlling the fixing means, the holding means, the driving means, the first medium voltage applying means, and the second medium voltage applying means.

20. The sample separation apparatus as set forth in claim 18, further comprising a first electrode, a second electrode, and a second wiring means for connecting the first electrode and the second electrode to the second medium voltage applying means.

21. The sample separation apparatus as set forth in claim 20, further comprising a first buffer solution chamber filled with a first buffer solution and a second buffer solution chamber filled with a second buffer solution, wherein: the holding means holds the first electrode and the second electrode, and the driving means disposes the first electrode and the second electrode in the first buffer solution chamber and the second buffer solution chamber respectively.

22. The sample separation apparatus as set forth in claim 21, further comprising a temperature sensor for detecting a temperature of the second medium or the first or second buffer solutions which is in contact with the second medium.

23. The sample separation apparatus as set forth in claim 20, wherein a first direction separation instrument for separating the sample in the first medium in the first direction is further fixed.

24. The sample separation apparatus as set forth in claim 23, wherein the first direction separation instrument includes a first separation chamber for performing a first separation.

25. The sample separation apparatus as set forth in claim 24, further comprising a third electrode, wherein the third electrode for electrifying the first medium is fixed on the first separation chamber.

26. The sample separation apparatus as set forth in claim 25, further comprising a first medium voltage applying means for applying a voltage to the first medium.

27. The sample separation apparatus as set forth in claim 26, further comprising a first wiring means for connecting the third electrode to the first medium voltage applying means.

28. The sample separation apparatus as set forth in claim 26, wherein the third electrode is held by the holding means and is disposed in the first separation chamber by the driving means.

29. The sample separation apparatus as set forth in claim 23, wherein the first direction separation instrument further includes a plurality of reagent chambers.

30. The sample separation apparatus as set forth in claim 29, wherein the driving means reciprocates the holding means in the direction parallel or perpendicular to the plane with the first medium being immersed in the plurality or reagent chambers.

31. The sample separation apparatus as set forth in claim 29, wherein a sealing sheet for sealing each reagent chamber filled with a reagent is provided.

32. The sample separation apparatus as set forth in claim 31, further comprising sheet peeling means for peeling the sealing sheet or further comprising sheet punching means for punching the sealing sheet, wherein said sheet peeling means or said sheet punching means is provided on the holding means.

33. The sample separation apparatus as set forth in claim 32, wherein the reagent chambers are partially or respectively filled with a plurality of reagents which are covered by the sealing sheet and which are separated from each other by the sealing sheet, and the plurality of reagents are mixed with each other by peeling or punching the sealing sheet.

* * * * *